US011497921B2

(12) United States Patent
Hahn et al.

(10) Patent No.: US 11,497,921 B2
(45) Date of Patent: *Nov. 15, 2022

(54) CARDIAC THERAPY SYSTEM USING SUBCUTANEOUSLY SENSED P-WAVES FOR RESYNCHRONIZATION PACING MANAGEMENT

(71) Applicant: CARDIAC PACEMAKERS, INC., St. Paul, MN (US)

(72) Inventors: Stephen J. Hahn, Shoreview, MN (US); Krzysztof Z. Siejko, Maple Grove, MN (US); William J. Linder, Golden Valley, MN (US); Keith R. Maile, New Brighton, MN (US); Amy Jean Brisben, St. Paul, MN (US); Keith L. Herrmann, Minneapolis, MN (US); Brendan E. Koop, Ham Lake, MN (US); Benjamin J. Haasl, Forest Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 445 days.

This patent is subject to a terminal disclaimer.

(21) Appl. No.: 16/681,103

(22) Filed: Nov. 12, 2019

(65) Prior Publication Data

US 2020/0094063 A1    Mar. 26, 2020

Related U.S. Application Data

(63) Continuation of application No. 15/633,517, filed on Jun. 26, 2017, now Pat. No. 10,512,784.

(Continued)

(51) Int. Cl.
*A61N 1/372* (2006.01)
*A61N 1/365* (2006.01)
(Continued)

(52) U.S. Cl.
CPC ........ *A61N 1/37288* (2013.01); *A61B 5/0006* (2013.01); *A61B 5/349* (2021.01);
(Continued)

(58) Field of Classification Search
CPC ............ A61N 1/37288; A61N 1/36514; A61N 1/365; A61N 1/3925; A61N 1/3756
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — William J Levicky
(74) *Attorney, Agent, or Firm* — Seager, Tufte & Wickhem LLP

(57) ABSTRACT

Systems, methods and implantable devices configured to provide cardiac resynchronization therapy and/or bradycardia pacing therapy. A first device located in the heart of the patient is configured to receive a communication from a second device and deliver a pacing therapy in response to or in accordance with the received communication. A second device located elsewhere is configured to determine an atrial event has occurred and communicate to the first device to trigger the pacing therapy. The second device may be configured for sensing the atrial event by the use of vector (Continued)

selection and atrial event windowing, among other enhancements. Exception cases are discussed and handled as well.

20 Claims, 21 Drawing Sheets

Related U.S. Application Data

(60) Provisional application No. 62/355,121, filed on Jun. 27, 2016.

(51) Int. Cl.
| | | |
|---|---|---|
| *A61N 1/375* | (2006.01) | |
| *A61N 1/39* | (2006.01) | |
| *A61B 5/00* | (2006.01) | |
| *A61B 5/349* | (2021.01) | |
| *A61N 1/362* | (2006.01) | |
| *A61N 1/368* | (2006.01) | |
| *A61B 5/352* | (2021.01) | |
| *A61B 5/363* | (2021.01) | |

(52) U.S. Cl.
CPC .............. *A61B 5/686* (2013.01); *A61N 1/365* (2013.01); *A61N 1/36514* (2013.01); *A61N 1/3756* (2013.01); *A61N 1/3925* (2013.01); *A61N 1/3962* (2013.01); *A61B 5/0031* (2013.01); *A61B 5/352* (2021.01); *A61B 5/363* (2021.01); *A61B 5/4836* (2013.01); *A61B 5/726* (2013.01); *A61N 1/3627* (2013.01); *A61N 1/3684* (2013.01); *A61N 1/36507* (2013.01); *A61N 1/3956* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Farjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,702,427 A | 12/1997 | Ecker et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |

(56) References Cited

U.S. PATENT DOCUMENTS

| | | |
|---|---|---|
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,471 B1 | 9/2001 | Bornzin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B1 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,505,077 B1 | 1/2003 | Kast et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,721,598 B1 | 4/2004 | Helland et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |

(56) References Cited

U.S. PATENT DOCUMENTS

| | | |
|---|---|---|
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,575 B2 | 12/2006 | Ostroff et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,189,204 B2 | 3/2007 | Ni et al. |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,376,458 B2 | 5/2008 | Palreddy et al. |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,477,935 B2 | 1/2009 | Palreddy et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Mmendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,340 B2 | 8/2010 | Sanghera et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,809,441 B2 | 10/2010 | Kane et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |

(56) References Cited

U.S. PATENT DOCUMENTS

| | | |
|---|---|---|
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | Disilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,079,959 B2 | 12/2011 | Sanghera et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,116,867 B2 | 2/2012 | Ostroff |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,157,813 B2 | 4/2012 | Ko et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,195,308 B2 | 6/2012 | Frank et al. |
| 8,200,341 B2 | 6/2012 | Sanghera et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,034 B2 | 12/2012 | Patangay et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,399 B2 | 7/2013 | Degroot et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,483,843 B2 | 7/2013 | Sanghera et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,878 B2 | 10/2013 | Allavatam et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |

(56) References Cited

U.S. PATENT DOCUMENTS

| | | |
|---|---|---|
| 8,626,294 B2 | 1/2014 | Sheldon et al. |
| 8,626,310 B2 | 1/2014 | Barror et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,325 B2 | 11/2014 | Boling et al. |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,072,914 B2 | 7/2015 | Greenhut et al. |
| 9,079,035 B2 | 7/2015 | Sanghera et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 9,993,171 B2 | 6/2018 | An et al. |
| 10,050,700 B2 | 8/2018 | Ludwig et al. |
| 10,213,610 B2 | 2/2019 | Maile et al. |
| 10,512,784 B2 * | 12/2019 | Hahn .................. A61N 1/3756 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |

(56) References Cited

U.S. PATENT DOCUMENTS

| | | |
|---|---|---|
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Edinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0275522 A1 | 11/2008 | Dong et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |

(56) References Cited

U.S. PATENT DOCUMENTS

| | | |
|---|---|---|
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0264949 A1 | 10/2009 | Dong et al. |
| 2009/0266573 A1 | 10/2009 | Engmark et al. |
| 2009/0270937 A1 | 10/2009 | Yonce et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023083 A1* | 1/2010 | Eisinger ............. A61N 1/3704 607/27 |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0305646 A1 | 12/2010 | Schulte et al. |
| 2010/0312309 A1 | 12/2010 | Harding |
| 2010/0331905 A1 | 12/2010 | Li et al. |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0178567 A1 | 7/2011 | Pei et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0029335 A1 | 2/2012 | Sudam et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0030484 A1 | 1/2013 | Zhang et al. |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0245709 A1 | 9/2013 | Bohn et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |

(56) References Cited

U.S. PATENT DOCUMENTS

| | | |
|---|---|---|
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0310890 A1 | 11/2013 | Sweeney |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0163631 A1 | 6/2014 | Maskara et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207013 A1 | 7/2014 | Lian et al. |
| 2014/0207149 A1 | 7/2014 | Hastings et al. |
| 2014/0207210 A1 | 7/2014 | Willis et al. |
| 2014/0214104 A1* | 7/2014 | Greenhut ............ A61N 1/3756 607/4 |
| 2014/0222098 A1 | 8/2014 | Baru et al. |
| 2014/0222099 A1 | 8/2014 | Sweeney |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236253 A1 | 8/2014 | Ghosh et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257421 A1 | 9/2014 | Sanghera et al. |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0032173 A1 | 1/2015 | Ghosh |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0142069 A1 | 5/2015 | Sambelashvili |
| 2015/0142070 A1 | 5/2015 | Sambelashvili |
| 2015/0157861 A1 | 6/2015 | Aghassian |
| 2015/0165199 A1 | 6/2015 | Karst et al. |
| 2015/0173655 A1 | 6/2015 | Demmer et al. |
| 2015/0182751 A1 | 7/2015 | Ghosh et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1* | 8/2015 | Stahmann ............ A61N 1/3756 607/25 |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297902 A1 | 10/2015 | Stahmann et al. |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0360036 A1 | 12/2015 | Kane et al. |
| 2015/0360041 A1 | 12/2015 | Stahmann et al. |
| 2016/0007873 A1 | 1/2016 | Huelskamp et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0045131 A1 | 2/2016 | Siejko |
| 2016/0045132 A1 | 2/2016 | Siejko |
| 2016/0045136 A1 | 2/2016 | Siejko et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0114162 A1 | 4/2016 | Sheldon et al. |
| 2016/0121127 A1 | 5/2016 | Klimovitch et al. |
| 2016/0121128 A1 | 5/2016 | Fishier et al. |
| 2016/0121129 A1 | 5/2016 | Persson et al. |
| 2016/0144190 A1* | 5/2016 | Cao .................... A61N 1/3756 607/17 |
| 2016/0151621 A1 | 6/2016 | Maile et al. |
| 2016/0175601 A1 | 6/2016 | Nabutovsky et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0271406 A1 | 9/2016 | Maile et al. |
| 2016/0277097 A1 | 9/2016 | Ludwig et al. |
| 2016/0296131 A1 | 10/2016 | An et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0021159 A1 | 1/2017 | Reddy et al. |
| 2017/0035315 A1 | 2/2017 | Jackson |
| 2017/0043173 A1 | 2/2017 | Sharma et al. |

(56) References Cited

U.S. PATENT DOCUMENTS

| | | |
|---|---|---|
| 2017/0043174 A1 | 2/2017 | Greenhut et al. |
| 2017/0056665 A1 | 3/2017 | Kane et al. |
| 2017/0056666 A1 | 3/2017 | Kane et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatam et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368360 A1 | 12/2017 | Hahn et al. |
| 2018/0008829 A1 | 1/2018 | An et al. |
| 2018/0008831 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0021584 A1 | 1/2018 | An et al. |
| 2018/0036527 A1 | 2/2018 | Reddy et al. |
| 2018/0056075 A1 | 3/2018 | Hahn et al. |
| 2018/0056079 A1 | 3/2018 | Hahn et al. |
| 2018/0078773 A1 | 3/2018 | Thakur et al. |
| 2018/0116593 A1 | 5/2018 | An et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |
| WO | 2016118735 A1 | 7/2016 |

OTHER PUBLICATIONS

International Search Report and Written Opinion dated Sep. 26, 2017 for International Application No. PCT/US2017039312.

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

* cited by examiner

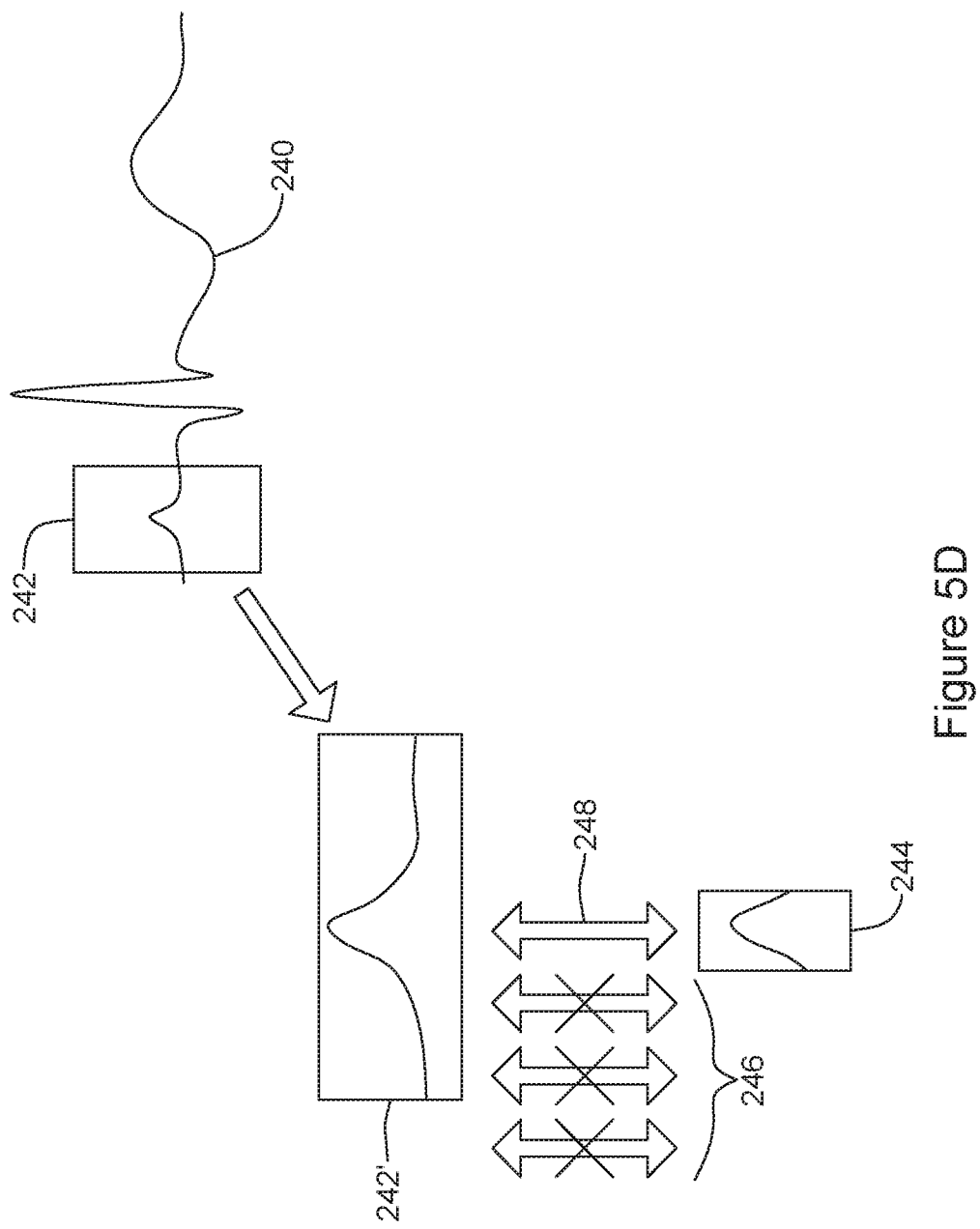

CARDIAC THERAPY SYSTEM USING SUBCUTANEOUSLY SENSED P-WAVES FOR RESYNCHRONIZATION PACING MANAGEMENT

CROSS REFERENCE TO RELATED APPLICATIONS

The present application is a continuation of U.S. patent application Ser. No. 15/633,517, filed Jun. 26, 2017 and titled CARDIAC THERAPY SYSTEM USING SUBCUTANEOUSLY SENSED P-WAVES FOR RESYNCHRONIZATION PACING MANAGEMENT, which claims the benefit of and priority to U.S. Provisional Patent Application Ser. No. 62/355,121, filed Jun. 27, 2016, the disclosures of which are incorporated herein by reference.

BACKGROUND

Cardiac resynchronization therapy (CRT) resynchronizes the electrical activation and therefore the contractions of the heart's chambers to enhance pumping efficiency. Benefits may include increased exercise capacity and reduced hospitalization and mortality. CRT devices operate by controlling or affecting the timing of contraction of one or more cardiac chambers relative to one or more other cardiac chambers. For example, contractions of one or more of the ventricle(s) may be timed relative to contraction of the atria, or contractions of the left and right ventricles may be timed relative to one another.

A "fusion" beat occurs when multiple activation signals affect the same tissue at the same time. For example, electrical fusion between pacing of one ventricle with spontaneous activation of another ventricle (for example, paced left ventricular activation and spontaneous right ventricular activation) produces a fusion beat. The generation of fusion beats is a goal of cardiac resynchronization in many circumstances.

Prior systems generally included intracardiac electrodes coupled via transvenous leads to an implanted pulse generator. The leads of such systems are widely known as introducing various morbidities and are prone to eventual conductor and/or insulator failure. The presence of leads and their known morbidities and failures in CRT systems likely reduce usage within the indicated population of heart failure patients.

Newer generation pacemakers include the leadless cardiac pacemaker (LCP), which can be implanted entirely within the heart and does not require a transvenous (or any) lead. Such devices are commercially available in certain placed, but are currently indicated for use in bradycardia pacing. The LCP also presents an opportunity to provide an alternative to traditional CRT therapy using transvenous leads. New and alternative systems, devices and methods directed at providing CRT therapy using the LCP are desired.

OVERVIEW

The present inventors have recognized, among other things, that a problem to be solved is the management of CRT using information gathered by plural implantable devices. In order to resynchronize behavior of the chambers of the heart that are poorly synchronized, it is necessary to understand what is occurring, and when, in different chambers. An LCP implanted in a single chamber of the heart may, in some examples, receive data transmitted from a separate device, such as another LCP or an extracardiac device such as a subcutaneous cardiac monitor, or a subcutaneous implantable cardiac defibrillator (SICD), and use the received data to time the delivery of a pacing pulse to a heart chamber. In an embodiment, the LCP receives an indication from an SICD that a P-wave, indicating atrial depolarization (which occurs relative to atrial contraction), has been detected by the SICD at a particular time, and the LCP responds to the communicated information and delivers a pacing pulse.

In another example, an LCP may receive a command to pace in response to analysis performed by a second device. In a specific example, an SICD may detect a P-wave, determine timing and/or other parameters relative to the P-wave, and the SICD may then command therapy by the LCP. In another example, an LCP may deliver pacing pulses according to a self-determining timing sequence, but may occasionally or periodically receive supplemental timing information from a second device such as an SICD. For example, an SICD may determine evoked response characteristics to ensure fusion beats are resulting; if no fusion is observed, the SICD may issue a communication to the LCP. In this example, the SICD or the LCP may determine corrective steps to take by adjusting timing or energy, or other characteristic of the delivered therapy.

In further examples, a patient may receive Bradycardia pacing by having an SICD detect a P-wave and communicate to an LCP. For example, a patient having an atrioventricular nodal block (AV block) may exhibit P-waves that do not conduct naturally to the ventricles, and the LCP located, for example, in the right ventricle, may respond to data communicated to it to deliver pacing pulses. The communication may occur with every beat or may be periodic or occasional to confirm operation and/or prompt timing enhancements A first non-limiting example takes the form of an implantable device system comprising: a first medical device configured to deliver a pacing therapy to the heart of a patient; and a second medical device configured to sense activity of the heart of the patient; wherein the first medical device is configured to receive communication from the second medical device; wherein the second medical device is configured to detect an atrial event in the heart of the patient and issue a communication to the first medical device; wherein the first medical device is configured to deliver therapy to the heart of the patient in response to the communication issued by the second medical device.

Additionally or alternatively, a second non-limiting example takes the form of a system as in the first non-limiting example, wherein the second medical device is configured for an initialization sequence for detecting the atrial event, the initialization sequence comprising: detecting at least first and second cardiac cycles of the patient; establishing a window for detection of the atrial event; wherein the second medical device is configured to observe cardiac signals of the patient during the window for detection of the atrial event in order to detect the atrial event.

Additionally or alternatively, a third non-limiting example takes the form of a system as in the second non-limiting example, wherein the second medical device is configured to establish the window for detection of the atrial event relative to a feature of a ventricular event.

Additionally or alternatively, a fourth non-limiting example takes the form of a system as in the second non-limiting example, wherein the second medical device is configured to detect or determine occurrence of a therapy output by the first medical device, and to establish the window for detection of the atrial event relative to a therapy output by the first medical device.

Additionally or alternatively, a fifth non-limiting example takes the form of a system as in the second non-limiting example, wherein the second medical device is configured to calculate a composite cardiac cycle data set using the at least first and second cardiac cycles, and to establish the window for detection of the atrial event using the composite cardiac cycle data set.

Additionally or alternatively, a sixth non-limiting example takes the form of a system as in the second non-limiting example, wherein the initialization sequence further comprises determining characteristics for the atrial event, further wherein the second medical device is configured to use the characteristics determined during the initialization sequence in order to detect the atrial event.

Additionally or alternatively, a seventh non-limiting example takes the form of a system as in the sixth non-limiting example, wherein the characteristics for the atrial event comprise at least one of: an amplitude; a relative amplitude as compared to one or more preceding ventricular events; a relative amplitude as compared to a mean amplitude during a cardiac cycle; or a maximum or minimum slope.

Additionally or alternatively, an eighth non-limiting example takes the form of a system as in the second non-limiting example, wherein the second medical device is configured to determine whether a signal captured during the window for detection of the atrial event matches a stored atrial event template or a dynamic atrial event template.

Additionally or alternatively, a ninth non-limiting example takes the form of a system as in the first non-limiting example, wherein the second medical device comprises a plurality of electrodes configured for use in sensing cardiac signals, and the second medical device is configured to perform a sensing vector selection routine in which: the second medical device analyzes signals from a plurality of sensing vectors defined by the plurality of electrodes and selects a first sensing configuration for detection of ventricular events; and the second medical device analyzes signals from a plurality of sensing vectors defined by the plurality of electrodes and selects a second sensing configuration for detection of atrial events.

Additionally or alternatively, a tenth non-limiting example takes the form of a system as in the ninth non-limiting example, wherein the second medical device is configured to determine an atrial sensing window for detection of atrial events and is configured to selectively use the second sensing configuration to determine whether an atrial event takes place in the atrial sensing window.

Additionally or alternatively, an eleventh non-limiting example takes the form of a system as in the ninth non-limiting example, wherein the second medical device is configured to determine one or more parameters for sensing of atrial events using the second sensing configuration.

Additionally or alternatively, a twelfth non-limiting example takes the form of a system as in the ninth non-limiting example, wherein the second medical device is configured to establish a template for atrial events to use to determine whether a signal captured using the second sensing configuration is an atrial event of a predetermined type.

Additionally or alternatively, a thirteenth non-limiting example takes the form of a system as in any of the first to twelfth non-limiting examples, wherein the therapy is configured to treat bradycardia.

Additionally or alternatively, a fourteenth non-limiting example takes the form of a system as in any of the first to twelfth non-limiting examples, wherein the therapy is configured to improve cardiac synchronization and contraction efficacy.

Additionally or alternatively, a fifteenth non-limiting example takes the form of a system as in the fourteenth non-limiting example, wherein the communication is configured to indicate that the second medical device has detected the atrial event, and the first medical device is configured to determine when the therapy is to be delivered relative to timing of the atrial event.

Additionally or alternatively, a sixteenth non-limiting example takes the form of a system as in the fourteenth non-limiting example, wherein the communication is configured to command delivery of the therapy by the first device at a particular time.

Additionally or alternatively, a seventeenth non-limiting example takes the form of a system as in any of the first to sixteenth non-limiting examples, wherein the first medical device is a leadless cardiac pacemaker, and the second medical device is an implantable cardiac monitor.

Additionally or alternatively, an eighteenth non-limiting example takes the form of a system as in any of the first to sixteenth non-limiting examples, wherein the first medical device is a leadless cardiac pacemaker, and the second medical device is a subcutaneous implantable defibrillator.

Additional or alternatively, in a nineteenth non-limiting example, the present invention may take the form of methods for providing cardiac resynchronization therapy and/or bradycardia pacing therapy comprising using a system as in any of the first to eighteenth non-limiting examples.

A twentieth non-limiting example takes the form of an implantable medical device comprising: a plurality of implantable electrodes; operational circuitry for analyzing signals captured using the plurality of implantable electrodes; and communication circuitry for communicating to a second implantable medical device; wherein the operational circuitry is configured to perform a sensing vector selection routine in which: the operational circuitry analyzes signals from a plurality of sensing vectors defined by the plurality of electrodes and selects a first sensing configuration for detection of ventricular events; and the operational circuitry analyzes signals from a plurality of sensing vectors defined by the plurality of electrodes and selects a second sensing configuration for detection of atrial events; and further wherein: the operational circuitry is configured to use the second sensing configuration to determine whether an atrial event is detected; and in response to determining that an atrial event has been detected, the operational circuitry is configured to communicate to the second medical device.

Additionally or alternatively, a twenty-first non-limiting example takes the form of a system as in the twentieth non-limiting example, wherein the operational circuitry is configured to determine an atrial sensing window for detection of atrial events and is configured to selectively use the second sensing configuration to determine whether an atrial event takes place in the atrial sensing window, wherein the operational circuitry is configured to define the atrial sensing window in relationship to a ventricular sensed event sensed using the first sensing configuration.

Additionally or alternatively, a twenty-second non-limiting example takes the form of a system as in the twentieth non-limiting example, wherein the operational circuitry is configured to determine an atrial sensing window for detection of atrial events and is configured to selectively use the second sensing configuration to determine whether an atrial event takes place in the atrial sensing window, wherein the operational circuitry is configured to define the atrial sensing window in relationship to a detected therapy output by the second medical device.

Additionally or alternatively, a twenty-third non-limiting example takes the form of a system as in the twentieth non-limiting example, wherein the operational circuitry is configured to determine one or more parameters for sensing of atrial events using the second sensing configuration.

Additionally or alternatively, a twenty-fourth non-limiting example takes the form of a system as in the twentieth non-limiting example, wherein the operational circuitry is configured to establish a template for atrial events to use to determine whether a signal captured using the second sensing configuration is an atrial event of a predetermined type.

A twenty-fifth non-limiting example takes the form of an implantable medical device comprising: a plurality of implantable electrodes; operational circuitry for analyzing signals captured using the plurality of implantable electrodes; and communication circuitry for communicating to a second implantable medical device; wherein the operational circuitry is configured to perform an initialization sequence for detecting the atrial event, the initialization sequence comprising: detecting at least first and second cardiac cycles of the patient; establishing a window for detection of the atrial event; wherein the operational circuitry is configured to observe cardiac signals of the patient during the window for detection of the atrial event in order to detect the atrial event.

Additionally or alternatively, a twenty-sixth non-limiting example takes the form of a system as in the twenty-fifth non-limiting example, wherein the operational circuitry is configured to establish the window for detection of the atrial event relative to a feature of a ventricular event.

Additionally or alternatively, a twenty-seventh non-limiting example takes the form of a system as in the twenty-fifth non-limiting example, wherein the operational circuitry is configured to detect or determine occurrence of a therapy output by the second medical device, and to establish the window for detection of the atrial event relative to a therapy output by the second medical device.

Additionally or alternatively, a twenty-eighth non-limiting example takes the form of a system as in the twenty-fifth non-limiting example, wherein the operational circuitry is configured to calculate a composite cardiac cycle data set using the at least first and second cardiac cycles, and to use the composite cardiac cycle data set to establish the window for detection of the atrial event.

Additionally or alternatively, a twenty-ninth non-limiting example takes the form of a system as in the twenty-fifth non-limiting example, wherein operational circuitry is configured such that the initialization sequence further comprises determining characteristics for the atrial event, further wherein the operational circuitry is configured to determine use the characteristics determined during the initialization sequence in order to detect the atrial event.

Additionally or alternatively, a thirtieth non-limiting example takes the form of a system as in the twenty-fifth non-limiting example, wherein the operational circuitry is configured such that the characteristics for the atrial event comprise at least one of: an amplitude; a relative amplitude as compared to one or more preceding ventricular events; a relative amplitude as compared to a mean amplitude during a cardiac cycle; or a maximum or minimum slope.

Additionally or alternatively, a thirty-first non-limiting example takes the form of a system as in the twenty-fifth non-limiting example, wherein the operational circuitry is configured to determine whether a signal captured during the window for detection of the atrial event matches a stored atrial event template or a dynamic atrial event template.

Additionally or alternatively, a thirty-second non-limiting example takes the form of an implantable medical device system as in any of the twentieth to thirty-first non-limiting examples, wherein the first medical device is a subcutaneous implantable cardiac monitor, and the second medical device is a leadless cardiac pacemaker.

Additionally or alternatively, a thirty-third non-limiting example takes the form of an implantable medical device system as in any of the twentieth to thirty-first non-limiting examples, wherein the first medical device is a subcutaneous implantable cardiac defibrillator, and the second medical device is a leadless cardiac pacemaker.

Additionally or alternatively, a thirty-fourth non-limiting example takes the form of a method of treating a patient comprising providing cardiac resynchronization therapy by using a system as in any of the twentieth to thirty-third non-limiting examples.

Additionally or alternatively, a thirty-fifth non-limiting example takes the form of a method of treating a patient comprising providing bradycardia pacing therapy by using a system as in any of the twentieth to thirty-third non-limiting examples.

This is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 5C-5D illustrate methods of detecting a P-wave;

DETAILED DESCRIPTION

The following description should be read with reference to the drawings. The description and the drawings, which are not necessarily to scale, depict illustrative embodiments and are not intended to limit the scope of the disclosure.

Figure 1:
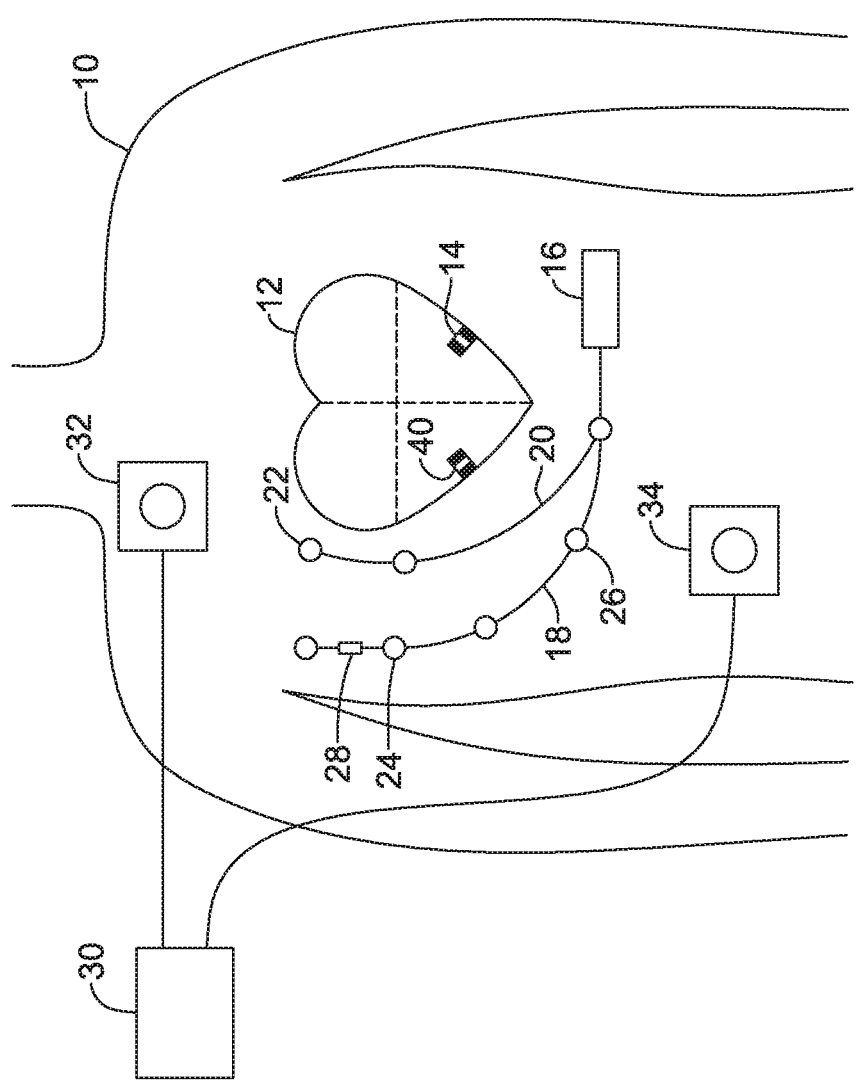
FIG. 1 illustrates a patient having a plurality of implantable medical devices.

FIG. 1 illustrates a patient 10 with a first implanted medical device, shown as a leadless cardiac pacemaker (LCP) 14 implanted inside the heart 12, in the left ventricle for illustrative purposes. The LCP 14 may be implanted in other chambers, such as the right ventricle or in the atrium, and more than one LCP may be provided.

A second medical device in the form of a subcutaneous implantable defibrillator (SICD) 16 having a left axillary canister and a lead having a bifurcation to provide two fingers, at 18 and 20. The lead includes a plurality of electrodes such as button or ring electrodes at 20, 22, 24 and 26, and may also include one or more coil electrodes as shown at 28.

The illustration in FIG. 1 shows a bifurcation in the lead 18/20; in other embodiments a simpler lead may be provided having a single elongated member with a plurality of electrodes thereon such as shown, for example, in U.S. Pat. No. 9,079,035, titled ELECTRODE SPACING IN A SUBCUTANEOUS IMPLANTABLE CARDIAC STIMULUS DEVICE, the disclosure of which is incorporated herein by reference. Rather than bifurcation, plural leads may be provided as shown, for example, in U.S. Pat. No. 7,149,575, titled SUBCUTANEOUS CARDIAC STIMULATOR DEVICE HAVING AN ANTERIORLY POSITIONED ELECTRODE.

The lead 18/20 may be implanted entirely subcutaneously, such as by extending across the anterior or posterior of the chest, or by going partly across the chest in a lateral/medial direction and then superiorly toward the head along the sternum. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference. A substernal placement may be used instead, with one finger 18/20 or the entire distal end of the lead (that is, the end distant from the canister 16) going beneath the sternum such as in US PG Patent Pub. No. 2017/0021159, titled SUBSTERNAL PLACEMENT OF A PACING OR DEFIBRILLATING ELECTRODE, the disclosure of which is incorporated herein by reference.

The devices 14 and 16 may communicate with one another and or with an external programmer 30. The programmer 30 may optionally use a wand (not shown) and/or skin electrodes 32 and 34 to facilitate communication. For example, skin electrodes 32 may be used for conducted communication with an implantable device. Conducted communication is communication via electrical signals which propagate via patient tissue and are generated by more or less ordinary electrodes. By using the existing electrodes of the implantable devices, conducted communication does not rely on an antenna and an oscillator/resonant circuit having a tuned center frequency or frequencies common to both transmitter and receiver.

For other communication approaches such as RF or inductive communication, the programmer 30 may use a programming wand or may have an antenna integral with the programmer 30 housing for communication. Though not shown in detail, the programmer 30 may include any suitable user interface, including a screen, buttons, keyboard, touchscreen, speakers, and various other features widely known in the art.

Subcutaneous implantable defibrillators may include, for example, the Emblem S-ICD System™ offered by Boston Scientific Corporation. Combinations of subcutaneous defibrillators and LCP devices are discussed, for example, in US PG Patent Publication Nos. 20160059025, 20160059024, 20160059022, 20160059007, 20160038742, 20150297902, 20150196769, 20150196758, 20150196757, and 20150196756, the disclosures of which are incorporated herein by reference. The subcutaneous defibrillator and LCP may, for example, exchange data related to cardiac function or device status, and may operate together as a system to ensure appropriate determination of cardiac condition (such as whether or not a ventricular tachyarrhythmia is occurring), as well as to coordinate therapy such as by having the LCP deliver antitachycardia pacing in an attempt to convert certain arrhythmias before the subcutaneous defibrillator delivers a defibrillation shock.

In several examples which follow, the focus is on creating effective CRT therapy through the cooperation of at least two devices 14, 16. In other examples that may use similar concepts for pacing with an LCP using information received from a second device, bradycardia pacing may instead be provided. Several of the below examples may be used to provide bradycardia pacing as a therapy for those with atrioventricular (AV) block, in which the electrical signals that cause contraction of the atria fail to be conducted to the ventricles. For such patients, the SICD 16 (or other second device, such as an atrially placed LCP or detection apparatus, or a subcutaneous monitor) may detect the P-wave and issue a communication to the LCP 14 commanding or requesting pace therapy, or simply indicating that the P-wave was noted.

In some examples, rather than a therapy device such as the subcutaneous defibrillator 16 shown in FIG. 1, a second implantable medical device may take the form of an implantable monitoring device. A cardiac monitor may be, for example, a loop monitor that captures data under select conditions using two or more sensing electrodes on a housing thereof and/or attached thereto with a lead. Such monitors have found use to assist in diagnosing cardiac conditions that may be infrequent or intermittent, or which have non-specific symptoms. For example, tracking unexplained systole or determining other cardiac conditions may be done with an implantable or even wearable cardiac monitor. In the context of the present invention, the implantable, or even wearable, cardiac monitor may be used in place of the subcutaneous defibrillator as described in any of the following examples.

Several examples focus on using a left ventricular LCP 14. However, some examples may instead use a right ventricular LCP 40, and other examples may include both the left ventricular LCP 14 and right ventricular LCP 40. For example, where the use of an LCP is mentioned relative to bradycardia pacing for patients with an AV block, there may be a right ventricular LCP, with or without the left ventricular LCP. In other examples, a three implant system may include two LCP devices 14, 40, as well as a subcutaneous device such as the SICD 16. In still other examples, an atrial-placed LCP (not shown) may also be included.

Figure 2:
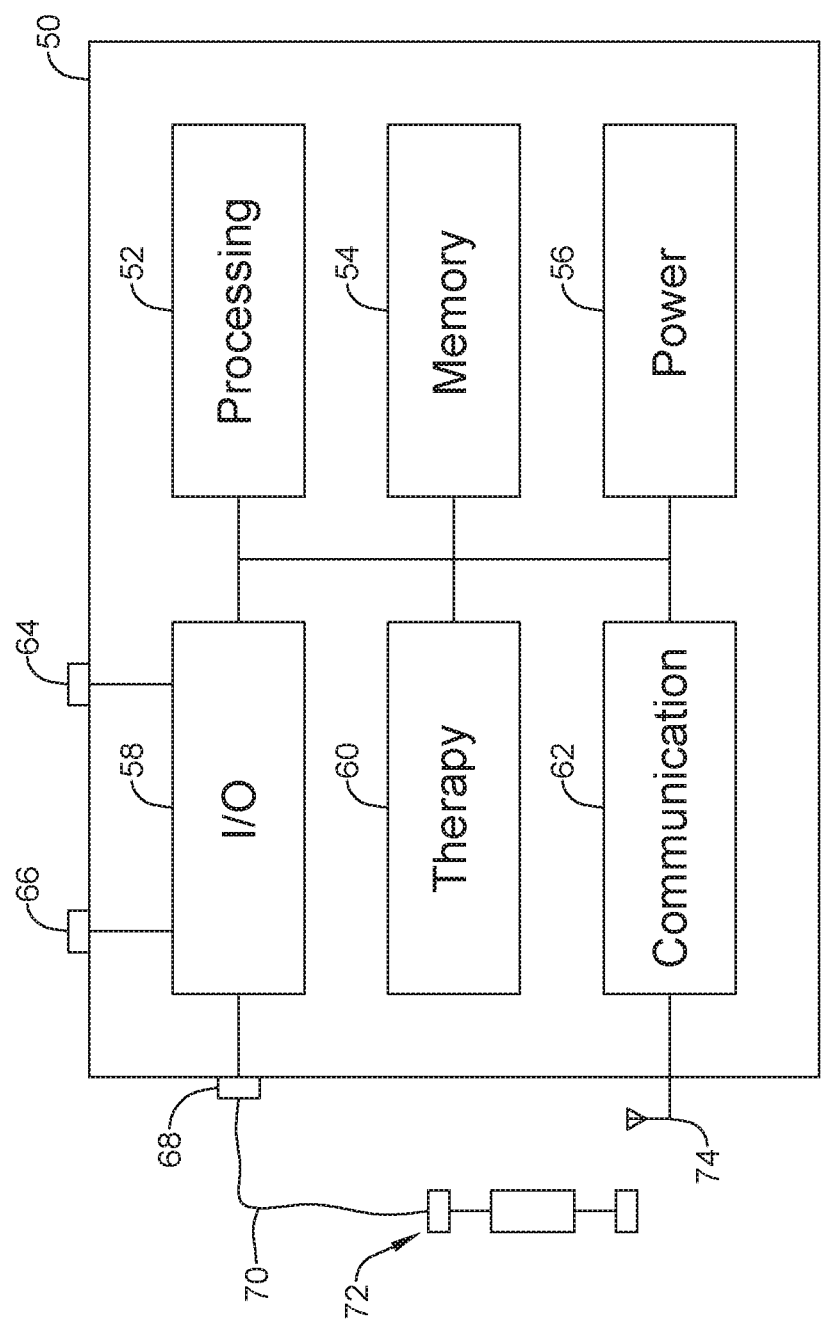
FIG. 2 illustrates a block diagram of an implantable medical device.

FIG. 2 illustrates a block diagram of an implantable medical device. The illustration indicates various functional blocks within a device 50, including a processing block 52, memory 54, power supply 56, input/output circuitry 58, therapy circuitry 60, and communication circuitry 62. These functional blocks make up the operational circuitry of the device. The I/O circuitry 58 can be coupled to one or more electrodes 64, 66 on the device 50 housing, and may also couple to a header 68 for attachment to one or more leads 70 having additional electrodes 72. The communication circuitry 62 may be coupled to an antenna 74 for radio communication (such as Medradio, ISM, or other RF), or alternatively to a coil for inductive communication, and/or may couple via the I/O circuitry 58 to a combination of electrodes 64, 66, 72, for conducted communication.

The processing block 52 will generally control operations in the device 50 and may include a microprocessor or microcontroller and/or other circuitry and logic suitable to its purpose. Processing block 52 may include dedicated circuits or logic for device functions such as converting analog signals to digital data, processing digital signals, detecting events in a biological signal, etc. The memory block may include RAM, ROM, flash and/or other memory circuits for storing device parameters, programming code, and data related to the use, status, and history of the device 50. The power supply 56 typically includes one to several batteries, which may or may not be rechargeable depending on the device 50. For rechargeable systems there would additionally be charging circuitry for the battery (not shown).

The I/O circuitry 58 may include various switches or multiplexors for selecting inputs and outputs for use. I/O circuitry 58 may also include filtering circuitry and amplifiers for pre-processing input signals. In some applications the I/O circuitry will include an H-Bridge to facilitate high power outputs, though other circuit designs may also be used. Therapy block 60 may include capacitors and charging circuits, modulators, and frequency generators for providing electrical outputs. An implantable monitoring apparatus may omit the therapy block 60 and may have a simplified I/O circuitry used simply to capture electrical or other signals such as chemical or motion signals.

Communications circuitry 62 may include a frequency generator/oscillator and mixer for creating output signals to transmit via the antenna 74. Some devices 50 may include a separate or even off-the shelf ASIC for the communications circuitry 62, for example. For devices using an inductive communication output, an inductive coil may be included. Devices may also use optical or acoustic communication approaches, and suitable circuits, transducers, generators and receivers may be included for these modes of communication as well or instead of those discussed above.

As those skilled in the art will understand, additional circuits may be provided beyond those shown in FIG. 2. For example, some devices 50 may include a Reed switch, Hall Effect device, or other magnetically reactive element to facilitate magnet wakeup, reset, or therapy inhibition of the device by a user, or to enable an MRI protection mode. A device lacking a lead may have plural electrodes on the housing thereof, as indicated at 64, 66, but may omit the header 64 for coupling to lead 70. In one example, a leadless device may use a header to couple to an electrode support feature that is attached to or wraps around the device housing.

Figure 3:
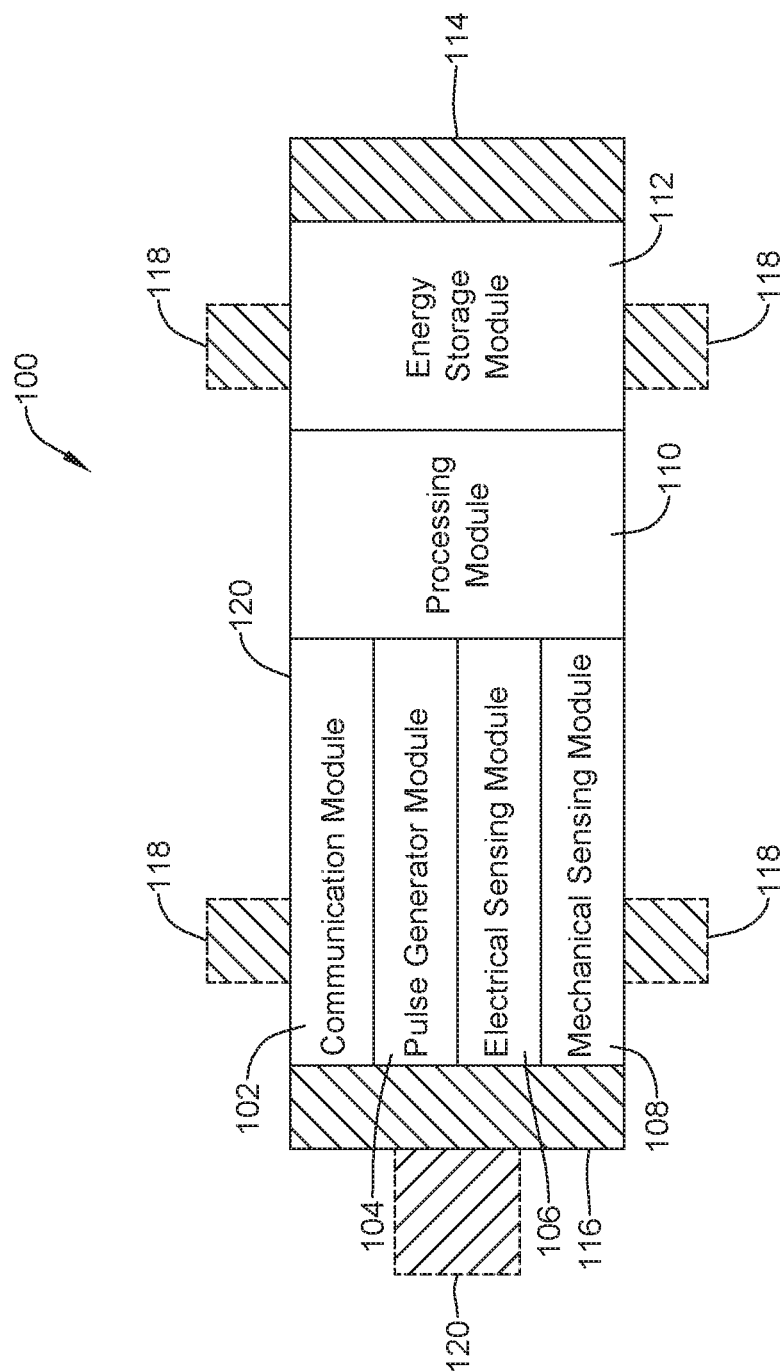
FIG. 3 shows an illustrative implantable leadless cardiac pacemaker.

FIG. 3 shows an illustrative LCP design. The LCP 100 is shown as including several functional blocks including a communications module 102, a pulse generator module 104, an electrical sensing module 106, and a mechanical sensing module 108. A processing module 110 may receive data from and generate commands for outputs by the other modules 102, 104, 106, 108. An energy storage module is highlighted at 112 and may take the form of a rechargeable or non-rechargeable battery, or a supercapacitor, or any other suitable element. Various details of the internal circuitry, which may include a microprocessor or a state-machine architecture, are further discussed in US PG Patent Publications 20150360036, titled SYSTEMS AND METHODS FOR RATE RESPONSIVE PACING WITH A LEADLESS CARDIAC PACEMAKER, 20150224320, titled MULTI-CHAMBER LEADLESS PACEMAKER SYSTEM WITH INTER-DEVICE COMMUNICATION, 20160089539, titled REFRACTORY AND BLANKING INTERVALS IN THE CONTEXT OF MULTI-SITE LEFT VENTRICULAR PACING, and 20160059025, titled, MEDICAL DEVICE WITH TRIGGERED BLANKING PERIOD, as well as other patent publications. Illustrative architectures may also resemble those found in the Micra™ (Medtronic) or Nanostim™ (St. Jude Medical) leadless pacemakers.

The device is shown with a first end electrode at 114 and a second end electrode at 116. A number of tines 118 may extend from the device in several directions. The tines 118 maybe used to secure the device in place within a heart chamber. Another attachment structure is shown at 120 and may take the form of a helical screw, if desired. In some examples, tines 118 are used as the only attachment features. Tissue attachment and retrieval features may be included in the LCP including those features shown in US PG Patent Publications 20150051610, titled LEADLESS CARDIAC PACEMAKER AND RETRIEVAL DEVICE, and 20150025612, titled SYSTEM AND METHODS FOR CHRONIC FIXATION OF MEDICAL DEVICES, the disclosures of which are incorporated herein by reference. Fixation and retrieval structures may instead resemble that of the Micra™ (Medtronic) or Nanostim™ (St. Jude Medical) leadless pacemakers.

Figure 4:
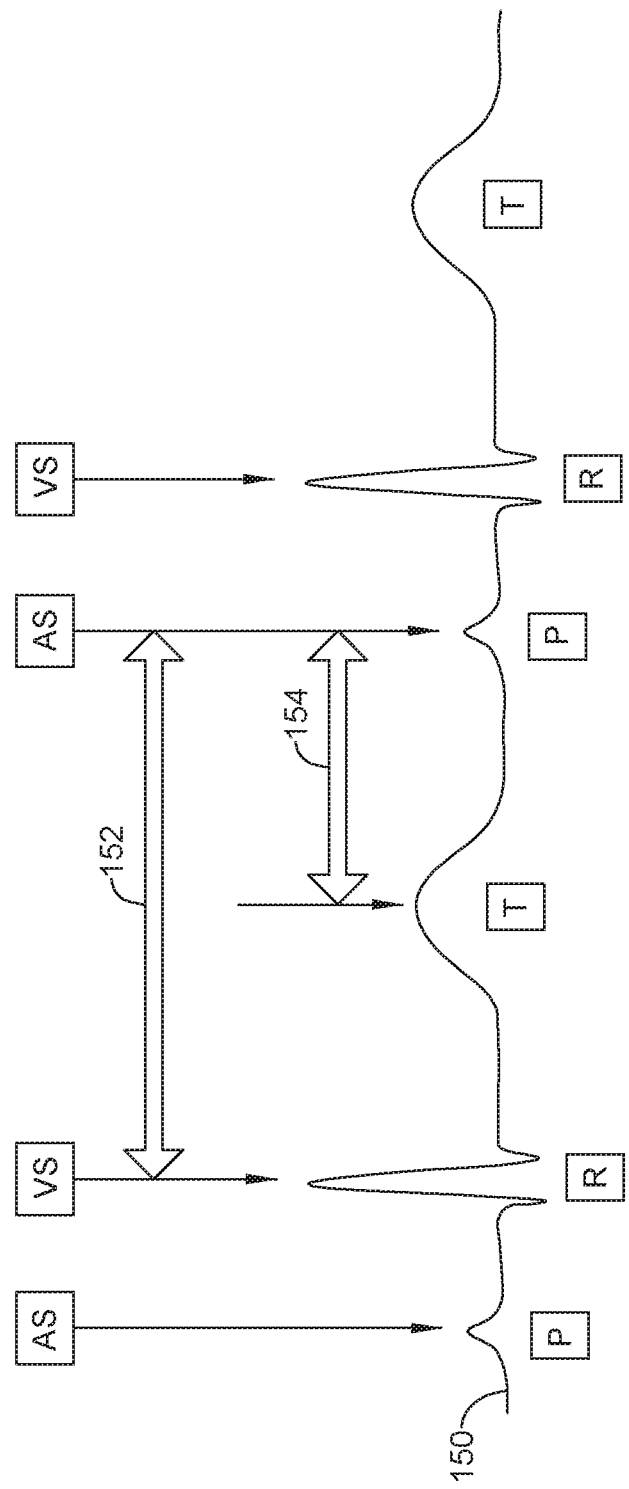
FIG. 4 shows an illustrative cardiac signal.

FIG. 4 shows an illustrative cardiac signal. A far field representation (that is, a signal captured using only electrodes that are neither in nor on the heart) is shown with trace 150. The trace 150 is marked using standard convention with the P-wave, R-wave (which, when combined with preceding Q-wave and following S-wave may be referred to as the QRS complex), and later T-wave. The P-wave represents atrial depolarization associated with atrial contraction to load the ventricles, the R-wave or QRS complex represents ventricular depolarization associated with the ventricles contracting to pump blood to the body and lungs, and the T-wave is associated with the electrical activity that repolarizes the ventricular muscle in preparation for a next beat. With heart failure and/or dyssynchrony, the timing of these individual events may be anomalous or abnormal, and the shape of depolarization waves can be different from that show as by, for example, having a much wider QRS complex or R-wave.

With traditional systems having transvenous leads, the intracardiac electrodes are placed to detect the atrial depolarization while also delivering resynchronizing pacing therapy to one or both ventricles. As a result, the circuitry of a single device would receive, directly, information for the P-wave allowing delivery at a timed interval of a pacing pulse to resynchronize contractions and improve pumping efficiency. However, with a system as in FIG. 1, the LCP may be unable to identify the P-wave generated in the atria from an implanted location in the ventricle. Therefore the LCP, in several embodiments of the present invention, relies on a second medical device such as a subcutaneous cardiac monitor or SICD to determine whether and when the P-wave occurs. However, to facilitate such interaction, the present inventors have identified several potential optimizations.

For example, the SICD (or subcutaneous cardiac monitor) may be optimized for detection of R-waves and/or QRS complexes, in order to ensure that deadly arrhythmias (ventricular fibrillation and/or polymorphic ventricular tachycardia) can be appropriately and quickly identified. P-waves may be detected using separate parameters and/or analysis from R-wave detection for such a device. In some examples, a time window for P-wave detection is defined during which the SICD may specifically look for the P-wave. Such windows may be defined by analysis of the cardiac signals obtained from a patient using, for example, a ventricular event such as the R-wave/QRS complex or the T-wave as the starting point for timing delays 152, 154 shown in FIG. 4. Durations 152, 154 may be dynamic to adjust to the overall beat rate of the patient using data gathered from a patient or using a formula or accepted relationship.

Another optimization may include having the SICD (or subcutaneous cardiac monitor) use a dedicated sensing configuration to separately detect ventricular events and a second, separately defined dedicated sensing configuration to separately detect atrial events. For example, the Emblem™ S-ICD system performs vector selection to identify a sensing vector having optimal R-wave amplitude and signal to noise ratio as a default vector for sensing the patient's cardiac rhythm, as disclosed for example in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843 SENSING VECTOR SELECTION IN A CARDIAC STIMULUS DEVICE WITH POSTURAL ASSESSMENT, the disclosures of which are incorporated herein by reference. Related concepts are also disclosed in US PG Patent Pub. Nos. 2017/0112399, 2017/0113040, 2017/0113050, and 2017/0113053, the disclosures of which are incorporated herein by reference. In an example, a second vector selection and/or sensing configuration process may be used to determine how the P-wave will be detected by a given device.

In further examples, filtering, gain, or other characteristics may be selected specific to P-wave detection. For example, if a ventricular event sensing channel uses a first passband, a P-wave sensing channel passband may be set to a different passband. For example, the R-wave or ventricular event passband may be set in the range of 3-40 Hz, or 9-40 Hz, or other setting. The P-wave passband may be set to a different range, for example, 0.5 to 20 Hz. Such band setting and selection may be partly contingent on reviewing the captured signal of either or both of ventricular and/or atrial events. Methods as discussed in US PG Patent Pub. No. 2017/0156617, titled AUTOMATIC DETERMINATION AND SELECTION OF FILTERING IN A CARDIAC RHYTHM MANAGEMENT DEVICE, the disclosure of which is incorporated herein by reference, may be used to select a sensing channel passband(s). In another example, a passband may be varied until signal amplitude for the desired atrial or ventricular feature begins to drop, at which an edge or corner of the passband may be set, to achieve a targeted, narrow passband. Thus a P-wave sensing or atrial sensing configuration may use a different frequency band than a corresponding R-wave sensing or ventricular event filter. Alternatively, a single passband may be set for use in each of atrial and ventricular sensing, or different pre-set ranges may be used for each of atrial and ventricular sensing Setting the sensing configuration for detecting P-waves may thus include either or both of setting a detection window and/or selecting a filter configuration. In addition, the actual manner of detecting the P-wave is defined in some illustrative examples as part of the sensing configuration. For example, the P-wave may be detected by comparing a detected signal to a fixed or time-varying amplitude threshold. In another example, the P-wave may be detected by comparing segments of captured signal to a template until a match is found or at timeout occurs. When a match is found a P-wave detection can be declared; if a timeout occurs, it may be concluded that the P-wave was not present or simply not seen. In some examples, more than one method of identifying P-waves may be available for use, and a most effective approach for a given patient may be selected. For example, if amplitude threshold and template match approaches to P-wave detection are available, a patient having highly variable amplitude signals may have his or her device configured to use the template match approach rather than an amplitude based approach.

In some examples, a possible P-wave is confirmed as such prior to generating an output communication. For example, a template of the P-wave may be defined and used to confirm whether a detected signal that crosses an amplitude threshold is in fact a P-wave by comparing the detected signal to the template. Such templates may be static and stored in memory, may be matched from one beat to the next by comparing a first in time P-wave to a next in time possible P-wave, or may be a hybrid of a stored template and fully dynamic template as by, for example, averaging in newly detected P-waves to a template.

In some examples, patients may be pre-screened for P-wave availability with the second medical device that is to be used for synchronizing LCP pacing. For example, it may well be that due to anatomical variations or other factors, some patients will have a well-defined P-wave providing a ready fiducial for the SICD or subcutaneous cardiac monitor to rely upon to prompt CRT therapy by an LCP. In other patients, the P-wave may be difficult to detect consistently. Thus a pre-screening process may be performed, either as an in-clinic test, or by having a patient use a Holter monitor or by implanting a subcutaneous cardiac monitor to ensure that the P-wave is readily identified consistently.

The below examples further illustrate these optimizations and give examples of how such optimizations may be incorporated in a combination system having an LCP and a second implantable device, such as an SICD or a subcutaneous cardiac monitor, to generate and communicate timing information to the LCP for CRT purposes. First, however, FIGS. 5A-5B, 6 and 7 will show additional details in relation to the detected cardiac electrical signal.

Figure 5A:
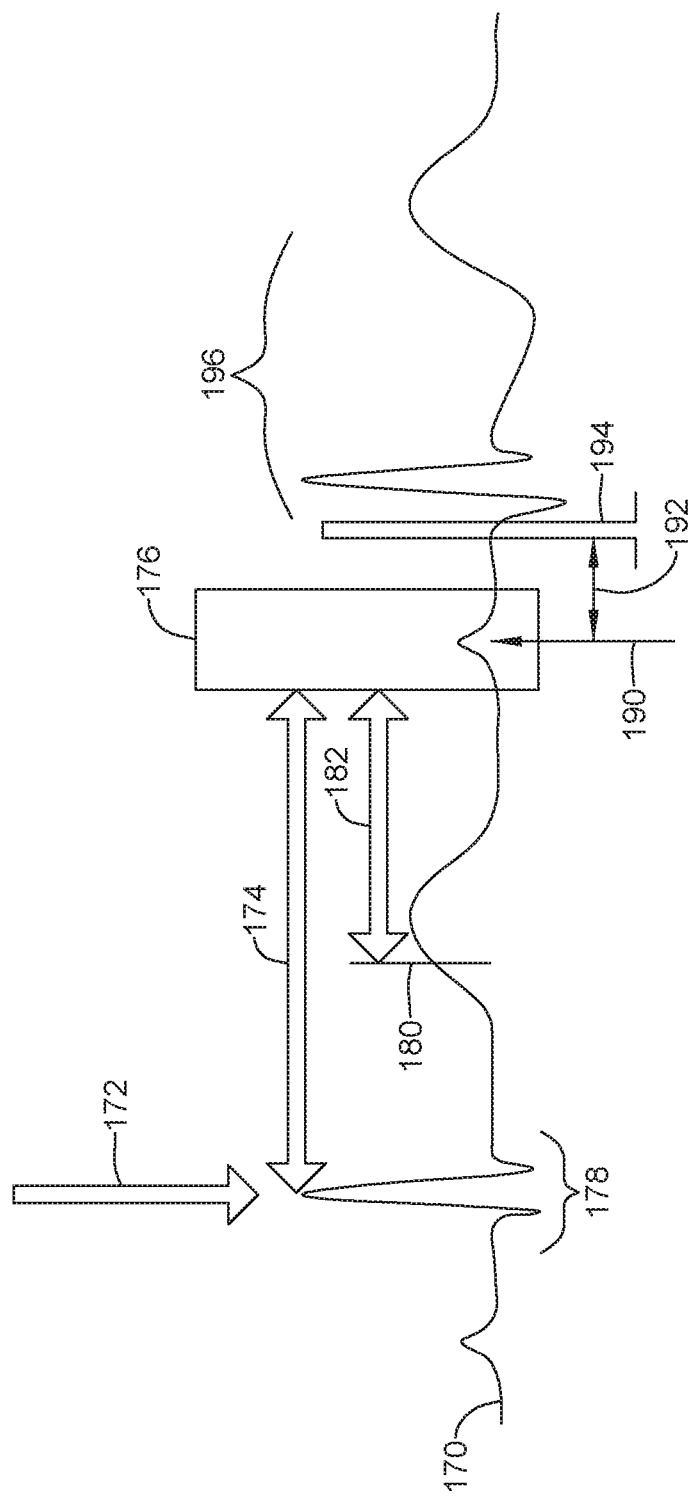
FIG. 5A shows another illustrative cardiac signal, this time with indications of a pacing therapy being delivered.

FIG. 5A shows another illustrative cardiac signal, this time with indications of a pacing therapy being delivered. The trace is shown at 170 with an intrinsic non-paced R-wave shown at 172. This R-wave at 172 is a fiducial for a time period 174 that defines a P-wave detection window at 176. In an alternative, a maximum positive slope point associated with the T-wave, indicated at 180, may serve as the fiducial for a duration 182 that again defines the P-wave detection window 176. In some examples, these interactions may be described by stating that a ventricular event is used to generate the fiducial for a window detection of the atrial event.

Figure 5B:
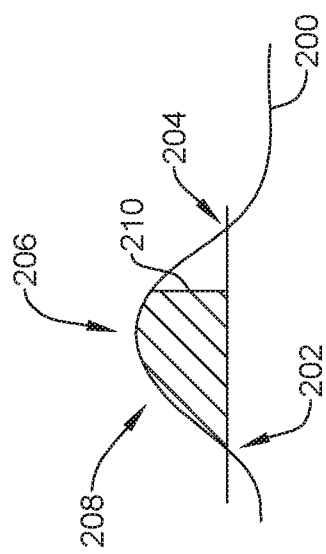
FIG. 5B shows example timing fiducials for a signal.

Various features of the signal 170 may serve as the fiducials for starting durations 174/182 in FIG. 5A. FIG. 5B shows example timing fiducials for a signal. A signal 200 may cross an amplitude threshold, creating a fiducial at 202 when going up, or another fiducial at 204 when coming back down. An amplitude peak 206 may instead be used. Alternatively, an inflection 208 may be used, with either positive slope or negative slope inflections available. In still another example, a fiducial 210 may rely on the area under the curve crossing a defined threshold. Any of these, or other, fiducials may be used to establish a point in time from which counting begins for purposes of defining a P-wave detection window. Fiducials may be applied to a prior P-wave, to a QRS complex, to an R-wave, or to the T-wave. The ST segment may be used if desired as by, for example, calculating a mid-point or other feature thereof.

Returning to FIG. 5A, if a P-wave is detected and, in some examples, confirmed within the P-wave detection window 176, another fiducial is set at 190 and, following a P-wave to pace delay 192, a pacing therapy is delivered as shown at 194. The delay 192 may be calculated by either the LCP that delivers the pace therapy or by the second device that provides a command to deliver therapy or other information indicating the occurrence of the P-wave. Such delay 192 may encompass and/or accommodate system latency (delays due to the time required to analyze data, make a decision, communicate data, receive communicated data, analyze the received data to determine the purpose of the communication, and generate therapy output).

For illustrative purposes, the pacing therapy 194 is shown as a monophasic, rectangular pulse, however, this is merely for illustration. The pacing pulse may be monophasic or biphasic, with the latter being more common than the former. Typical pace delivery can be either constant current or constant voltage, however, more complex waveforms such as ramped, exponential, and/or triphasic waveforms, or any other suitable waveform, may be used.

In the illustration shown, the pacing therapy 192 stimulates enough of the myocardium, either directly or by augmenting existing neural signals, to capture the heart. As a result, a QRS complex occurs causing beat 196. A brief visual comparison of QRS complex of beat 196 to the non-paced complex for beat 178 shows that, as is typical, the paced beat at 196 has a different shape or morphology than the intrinsic beat 178, with a more exaggerated Q-wave, and a differently shaped S-T segment. Other differences may be noted as is understood in the art. Such differences (or others) may be used, if desired, to aid in having a second device analyze the efficacy of CRT therapy delivered by an LCP.

Detection in the P-wave detection window may take several forms. The obtained cardiac signal may be compared to a P-wave detection threshold, which may be, for example, based on prior P-waves that have been detected. The obtained signal may be analyzed to determine whether a peak slope, combined with an amplitude, occurs. For example, the obtained signal may be analyzed for an upward slope of a select shape lasting for a minimum duration or minimum change in amplitude.

Figure 5C:
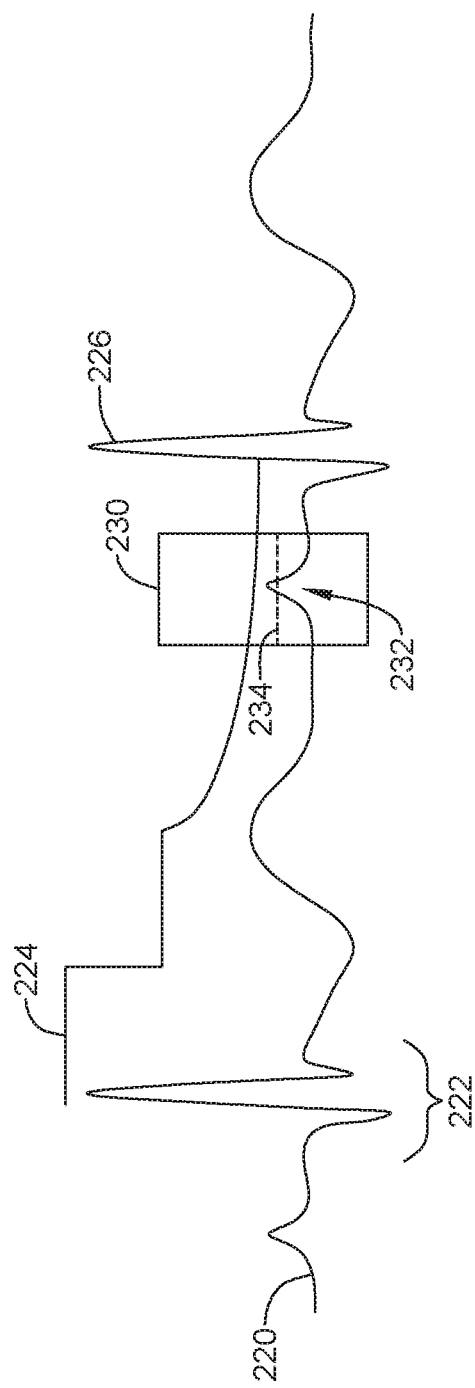

Two examples of P-wave detection are shown in FIGS. 5C and 5D. For example, as shown in FIG. 5C, a signal 220 comprises a first QRS complex at 222. A detection profile for R-wave detection is shown at 224 and may be a time-varying detection profile having a refractory period to pass over the QRS complex, followed by a constant threshold period to pass over the T-wave, followed by a decay period. Once the signal 220 crosses the detection profile 224, a new ventricular event detection is declared, in this case associated R-wave 226. The height of various parts of detection profile 224 may be calculated by reference to one or more previously detected R-waves as discussed in U.S. Pat. No. 8,565,878, for example. P-wave detection takes place in the P-wave detection window at 230. In this example, the P-wave 232 is detected when signal 220 crosses P-wave detection threshold 234. The P-wave detection threshold 234 may be set by reference to the amplitude of one or more previously detected P-waves. Alternatively, the P-wave detection threshold 234 may be scaled relative to the detection profile 224 (such as a 20% to 80%, or more or less of detection profile 224). The P-wave detection may then be used to trigger a pacing pulse (not shown) as described elsewhere in the present document.

FIG. 5D shows another example. Here, a cardiac signal is shown at 240 with a P-wave detection window at 242. The signal in window 242 is expanded as shown at 242'. A P-wave template is shown at 244. To detect the P-wave, a series of comparisons are made as incoming signal is received. Once enough signal is received to perform a morphology comparison, such as by difference of area, correlation waveform analysis, wavelet transform, or principal components analysis, for example, a morphology comparison is made. The morphology comparison is repeated as more signal comes in, with data entering a comparison window on a first-in, first-out basis, until a match is found at 248. Match 248 is then the P-wave detection.

In still further examples, a P-wave detection window 242 may be searched to identify a specific feature associated with a possible P-wave. For example, a P-wave may be identified by observing whether a slope in excess of a threshold and with a minimum pathlength occurs during the P-detection window. Additional ways to confirm that a signal is a P-wave are discussed relative to FIG. 6.

Figure 6:
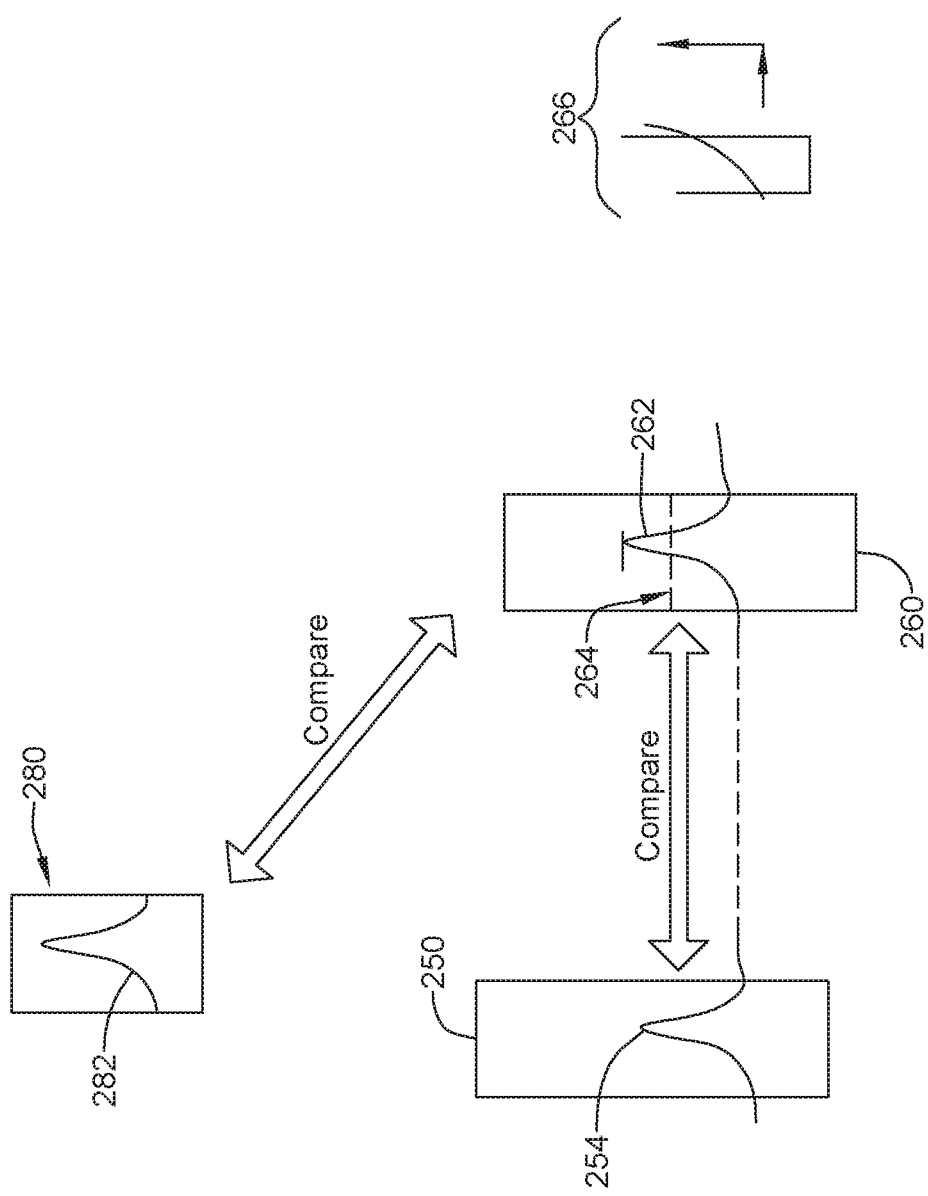
FIG. 6 illustrates ways that a signal feature may be analyzed.

FIG. 6 illustrates additional ways that a signal feature such as a P-wave may be analyzed for confirmation purposes. In the example of FIG. 6, a P-wave detection window is defined as shown at 260. The signal within the window 260, as shown at 262, includes a peak. In one example, to confirm that the signal within the window 260 is actually a P-wave, it may be analyzed for having at least a minimum amplitude 264. In another example, to confirm that the signal within the window 260 is a P-wave, slope characteristics such as a combination of rise and run may be analyzed, as shown at 266, where the rise is the amount of change of amplitude, and run is the duration within which the amplitude change occurs.

In still another example, matching, using for example a difference of area analysis, correlation waveform analysis, wavelet transform, or principal component analysis, may be used to compare the shape of peak 262 to another signal such as the shape of the signal in a prior P-wave detection window, shown at 250, using the signal shape therein 254 across all or a portion of the window 250. A beat-to-beat comparison may be termed a dynamic comparison, as the shape against which the newly detected possible P-wave is compared will change with each new cardiac cycle. In another example, a stored template, such as shown at 280, may be used. In this example, shape 262 would be compared against the shape 282 defined by the template 280. If a stored template does not change with time, it may be deemed a static template. A hybrid template may be configured to change slowly with time by averaging an existing data set with a newly detected and confirmed P-wave, or by averaging several preceding P-wave detections.

Figure 7:
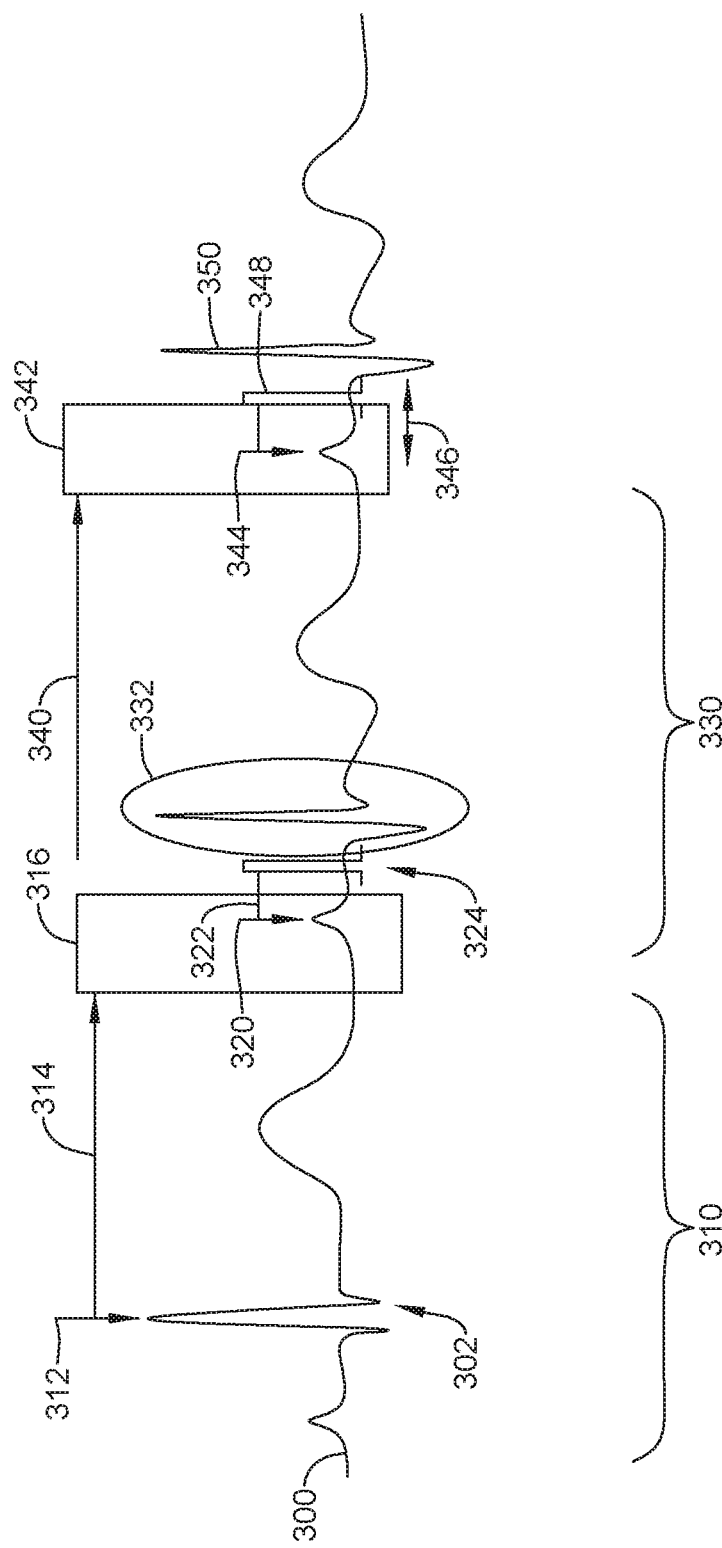
FIG. 7 shows another cardiac signal to illustrate operation of an embodiment.

FIG. 7 shows another cardiac signal to illustrate operation of an embodiment. In this example, the cardiac signal is shown at 300. A first cardiac cycle is shown at 310 including an intrinsic P-wave, non-paced QRS complex, and trailing T-wave. In the example, the R-wave peak is used as a fiducial at 312 to start a timer that expires with duration 314, triggering the start of a P-wave detection window 316. During the P-wave detection window 316, the SICD or subcutaneous cardiac monitor searches for a P-wave. The operation during the detection window 316 may include selecting a specific sensing configuration (sensing vector, filtering or the like) to observe for an atrial event such as the P-wave.

In the illustration of FIG. 7, an atrial sense occurs at 320, corresponding in this example to the peak amplitude of the P-wave. A delay is instituted at 322 prior to delivery of a ventricular pacing stimulus at 324. In one example, the delay 322 is a calculated delay, which may include a lag period to allow for analysis by the SICD or subcutaneous cardiac monitor, transmission of data or a command to an LCP, processing by the LCP, plus, if desired, some intentional delay to allow for appropriate timing of the pace pulse 324 to optimize pacing efficiency. For example, in a transvenous CRT system, an AV delay control may be used to institute appropriate delay from a P-wave or atrial event sense to the delivery of ventricular pacing therapy. In a system as disclosed herein, the AV delay can include both system lag as well as intentional delay.

A device may include special handling instructions for communication to the LCP during period 322, to count how many retries occur in the event that a communication message is not received or acknowledged appropriately. Thus, if for some reason (such as external interference), the initial communication from the SICD or subcutaneous cardiac monitor the LCP is not received, subsequent tries may indicate how many retries have occurred to allow the LCP to appropriately manage period 322. If there are multiple retries, the pacing pulse 324 may be inhibited, if desired, to avoid extending period 322 beyond a set limit. Rather than relying on a quantity of retries, the LCP may simply timeout.

Continuing the example, the P-wave at 320 is the start of a new cardiac cycle 330, which in this case now includes a paced QRS complex at 332 having a distinct morphology relative to the first complex 310. In this example, with a pace captured QRS complex 332, the device may alter its selection of fiducials to define a next P-wave detection window, shown at 342. For example, in FIG. 7, the delay 340 is now instituted from the pace delivery at 324, rather than the R-wave. The next atrial event or P-wave detection window is shown at 342. Again an atrial sense occurs at 344 at the peak of a P-wave, and following a delay 346 (which may again include both system lag and intentional delay), a pacing therapy pulse is delivered at 348 again causing a pace-captured QRS complex shown at 350. Depending on system settings, the delay at 346 may be the same as, or different from, the delay at 322, if desired.

Figure 8:
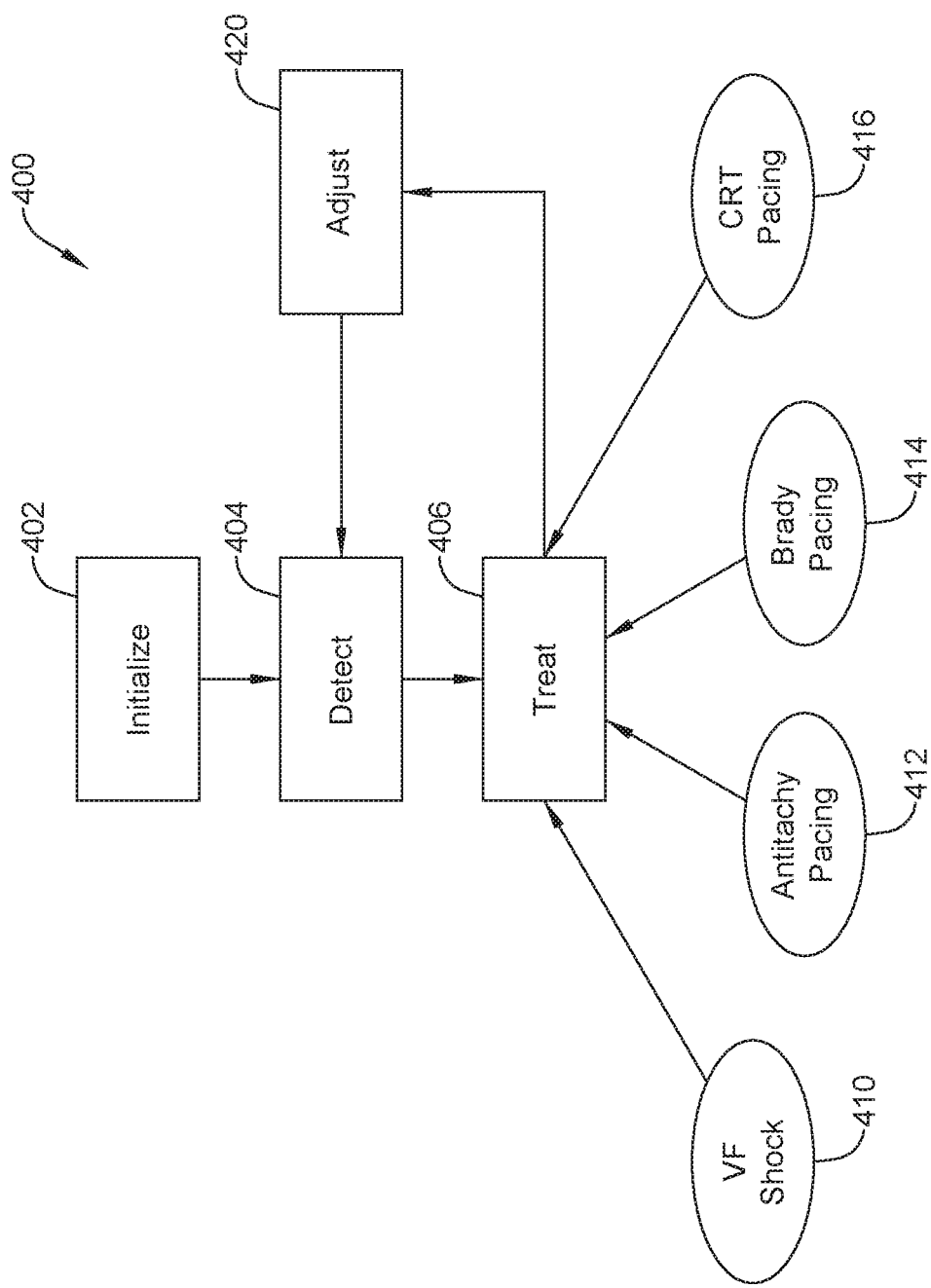
FIGS. 8, 9, and 10A-10B show block diagrams for illustrative examples.

FIGS. 8, 9, and 10A-10B show block diagrams for illustrative examples. In the example of FIG. 8, the overall method of using an implantable medical device is shown at 400. The device or system is initialized at 402, following which treatable conditions are detected at 404 and treatment is delivered at 406. For implantable cardiac systems such as shown in FIG. 1, treatment 406 may include delivering a therapy shock for ventricular fibrillation or polymorphic tachyarrhythmia, as indicated at 410. For example, an SICD may deliver a defibrillation shock at 410. Alternatively, antitachycardia pacing (ATP) may be delivered as shown at 412. For example, an LCP may deliver ATP in response to a request or command by an SICD, or of its own accord. An SICD may also deliver ATP if desired. Bradycardia pacing may be delivered by one or the other of an LCP or SICD, with the LCP likely being preferred due to the possible discomfort that SICD pacing delivery can cause the patient. In some examples, the Bradycardia pacing may be delivered to treat AV block using a right ventricular LCP. Finally, as detailed herein, CRT pacing may be delivered at 416.

Adjustments to the system configuration and other settings may be performed as indicated at 420, for example, in response to the various therapies 410, 412, 414, 416. For example, if CRT pacing 416 is delivered but fails to generate fusion beats, an adjustment may be made to the timing between P-wave detection and pacing delivery, or to the duration, amplitude, or other characteristics of the delivered pacing therapy. In another example if bradycardia pacing 414 is delivered but fails stimulate a ventricular contraction, the delivered therapy may be adjusted 420 by using a different amplitude, pulse width, or shape.

Returning to the initialization block, as discussed above and below, there may be several settings to configure during initialization 402. For example, sensing configuration (sense vectors and filtering, for example, for one or both of ventricular and/or atrial event detection) may be established during initialization to optimize sensing of ventricular and/or atrial events. Communication operations may be initialized as well, for example as discussed in U.S. patent application Ser. No. 15/070,013, titled COMMUNICATIONS IN A MEDICAL DEVICE SYSTEM WITH LINK QUALITY ASSESSMENT, and/or Ser. No. 15/058,412, titled COMMUNICATIONS IN A MEDICAL DEVICE SYSTEM WITH TEMPORAL OPTIMIZATION, the disclosures of which are incorporated herein by reference.

Figure 9:
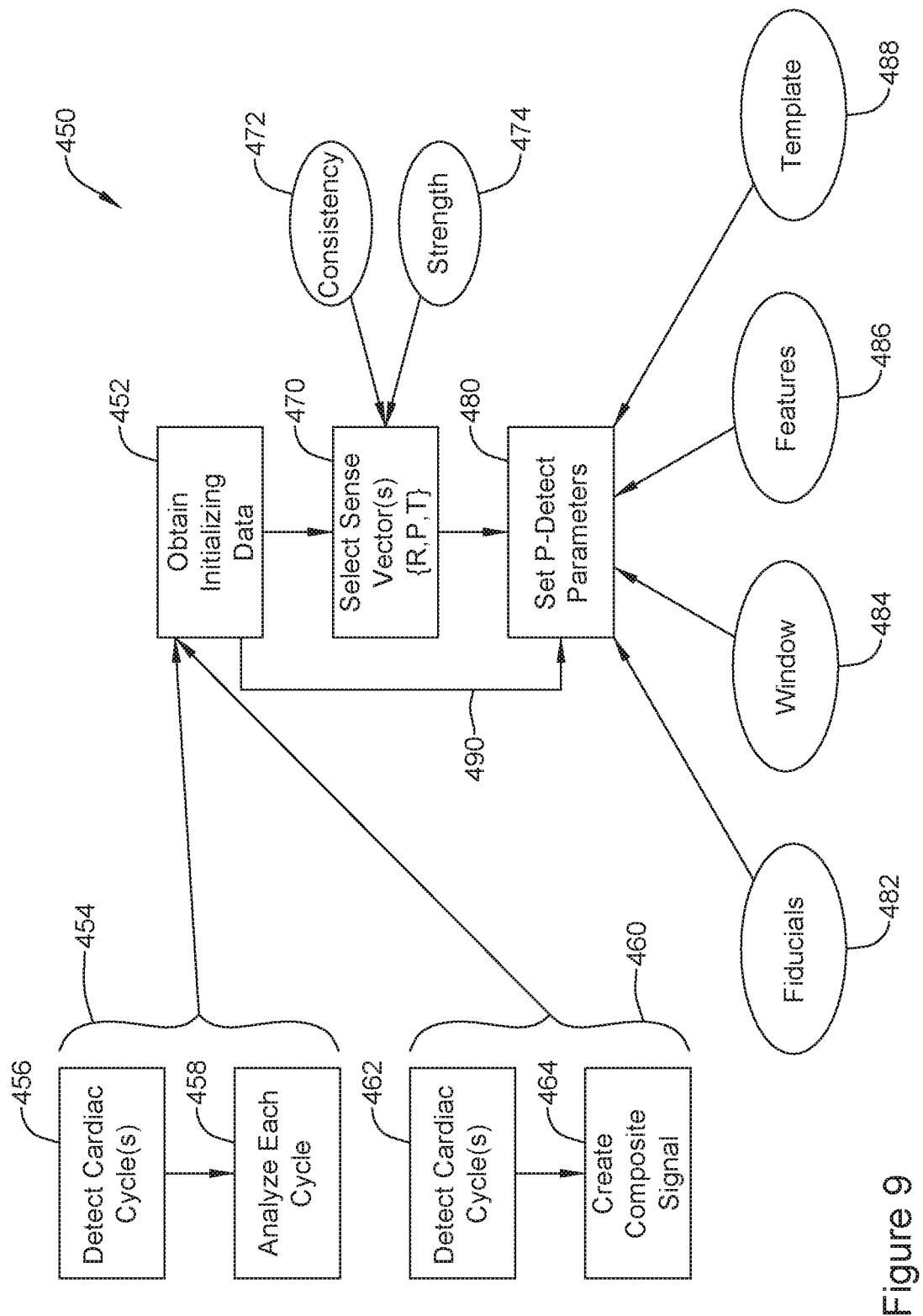

FIG. 9 shows a more detailed discussion of initialization relative to sensing parameters. In the example method 450, initializing data is obtained as indicated at 452, and one or more sensing vectors are selected, as indicated at 470. Next, the detection parameters such as parameters for detecting P-waves or atrial events (P-Detect Parameters) are set, as indicated at 480. Generally speaking, steps 452, 470 and 480 focus on the operations of the SICD or subcutaneous cardiac monitor for a system such as shown in FIG. 1 having both a subcutaneously located device along with an LCP. However, the LCP may also be setup for sensing configuration to optimize its ability to detect signals originating in whatever chamber of the heart the LCP is located in, and/or to filter out noise signals.

The step of obtaining initializing data at 452 may include various subprocesses as indicated on the left side of FIG. 9. For example, as indicated at 454, a plurality of individual cardiac cycles may be detected at 456 in one or several sensing vectors or with one or several different sensing configurations (affecting for example, filtering and/or amplification parameters, possibly in combination with vector selection parameters). The individual detections of cardiac cycles may be analyzed 458 by, for example, binning different detected data elements from each cycle as discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH. As an alternative shown at 460, a set of cardiac cycles are detected as indicated at 462 and a composite signal is generated as shown at 464. The use of a composite signal to establish sensing vector quality metrics is discussed, for example, in US PG Patent Pub. No. 2017/0113053, titled SIGNAL QUALITY MONITORING FOR MULTIPLE SENSE VECTORS IN CARDIAC DEVICES, the disclosure of which is incorporated herein by reference.

Next, in block 470, sense vector configurations for ventricular (targeting, for example, R waves, the QRS complex, and/or T-waves) and/or atrial event detection (targeting, for example, the P-wave) are selected. The vector configuration may include selecting combinations of electrodes to use, combinations of two or more vectors to use together, and/or the setting of filtering, blanking, refractory, amplification or other parameters. Various approaches to vector selection may be used including those referenced above from other patents or patent applications, as well as those discussed herein. For example, consistency of a vector configuration may be used, as indicated at 472, to select a given vector. Consistency 472 may mean, for example, that a selected cardiac event (P, R or T waves, or the QRS complex) is consistent in shape, amplitude and/or timing, in a given vector configuration. Alternatively or in combination with consistency, strength 474 of the signal, absolute and/or relative to noise may be considered as well.

In some examples, once vector configuration is set, the parameters for identifying P-waves are set as indicated at 480. In an alternative, as indicated by the line at 490, the sensing configuration step may be bypassed, and P-Detect parameters set at 480. For example, block 470 may be performed in some embodiments only when connected to a clinician programmer to ensure that appropriate signals are obtained and/or that sensing configuration is not modified contrary to known patient history, while blocks 452 and 480 may be performed by a device independent of programmer intervention. In some examples, on the other hand, block 480 may be omitted, with the sensing vector setup performed and any suitable method of P-wave detection used by the device without necessarily performing a separate optimization at 480.

Block 480 calls for setting one or more parameters to optimize P-wave detection. In some examples, this may include selecting one or more of the fiducials from which P-wave detection is triggered, at 482, setting a window for detecting the P-wave 484, selecting the features to look for when attempting to detect a P-wave 486, or selecting a template for P-wave confirmation at 488. Any of blocks 482, 484, 486, 488 may be used in various combinations or, in some examples, standing alone.

For example, the fiducial selection at 482 may be used to select a feature (whether atrial or ventricular, such as an R-wave, a T-wave, a preceding P-wave, or other physiological, such as a heart sound, a blood pressure signal, or other timing point of reference such as delivery of a pacing pulse), that starts a blanking period during which P-waves cannot be detected, for example, to pass over the T-wave, and upon expiration of the blanking period, P-wave detection is enabled. Alternatively, the fiducial 482 may be used to trigger the initiation of an analysis window for the P-wave. The window 484 may be used as shown above in FIGS. 5A, 6 and 7 by, for example, determining relative to a selected fiducial point when the P-wave typically appears and then setting a window of a duration equal or longer than the P-wave for allowing P-wave detection. The window may be, for example, about 50 to 400 milliseconds. In another example, the window may be about 100 to about 200 milliseconds. Other durations may be used.

Which features to use for identifying the P-wave is another element, as indicated at 486. For example, a P-wave may be identified by having an amplitude of a certain range, such as greater than a threshold. A threshold may be adaptive to current patient conditions by, for example, setting it to some percentage (50% to 90%, or more or less) of a preceding P-wave or an average of several preceding P-waves, or stored information relating to typical P-waves generally or specific to a given patient. Other features may include a maximum or minimum slope amplitude or length. In an example, the P-wave may be identified by the detected signal moving in a certain direction within predefined slope parameters for at least a predetermined amplitude or period of time. Thus, for example, the signal may have an upward slope that is characteristic of the P-wave, not so steep as for the R-wave, but steeper than the T-wave, of at least a select duration to avoid noise detection. Slope analysis may take place by using the first or second derivative of the obtained signal. Other features may be used instead at block 486.

The template 488 may also be used independent of other items to detect a P-wave. For example, the template may be compared to received data on a continuous or semi-continuous basis, and when a match is found, a P-wave may be declared (see FIG. 5d, above). The template may be an averaged composite of prior signals, or may be simply a prior P-wave, or may be constructed in any other suitable manner. The incoming signal itself may be a signal averaged composite of several cardiac cycles having, for example, P, Q, R and S signals (and T-waves if the composite is so configured).

In an example, during a window defined using 484, a template may be compared to an incoming data stream to identify a match. In other examples, the template 488 may be used to confirm a detected likely P-wave, such as a signal that crosses a defined amplitude threshold during a P-wave detection window. If the template 488 matches the likely P-wave, then P-wave detection is confirmed or, alternatively, if there is no match to the template 488, then the detection may be discarded as not being a P-wave.

Figure 10:
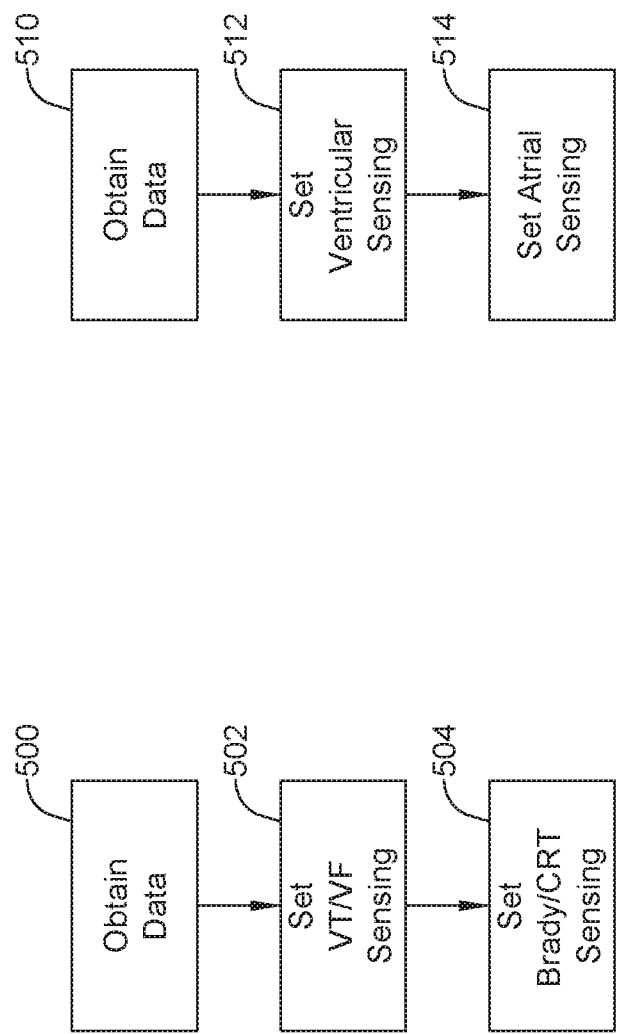

FIGS. 10A-10B show summary characterization of two approaches to sensing configuration. As shown in FIG. 10A, data is captured at 500. Next, VT/VF sensing 502 configuration and parameters are set by, for example, setting up sensing vectors and filtering, storing morphology information (templates, wavelet transforms or the like known in the art) for differentiating normal from abnormal cardiac activity, and the like. Finally, sensing configuration to be used for bradycardia therapy and/or CRT therapy control is set at 504. Block 504 may include configuring sensing vectors or combinations, filtering, and the like, as well as template selection, window setting and fiducial assessment, or other steps noted both above and below.

FIG. 10B shows another characterization. Here, data is obtained at 510, following by setting ventricular sensing parameters at 512. Ventricular sensing 512 parameters may be optimized to detect R-waves and/or VT/VF signals, including filtering and vector selection or combinations, as well as threshold setting and/or template formation. Atrial sensing parameters are set at 514, and may include optimization to detect P-waves or other atrial events including filtering, windowing and vector selection or combinations, as well as threshold setting and/or template formation.

Figure 11:
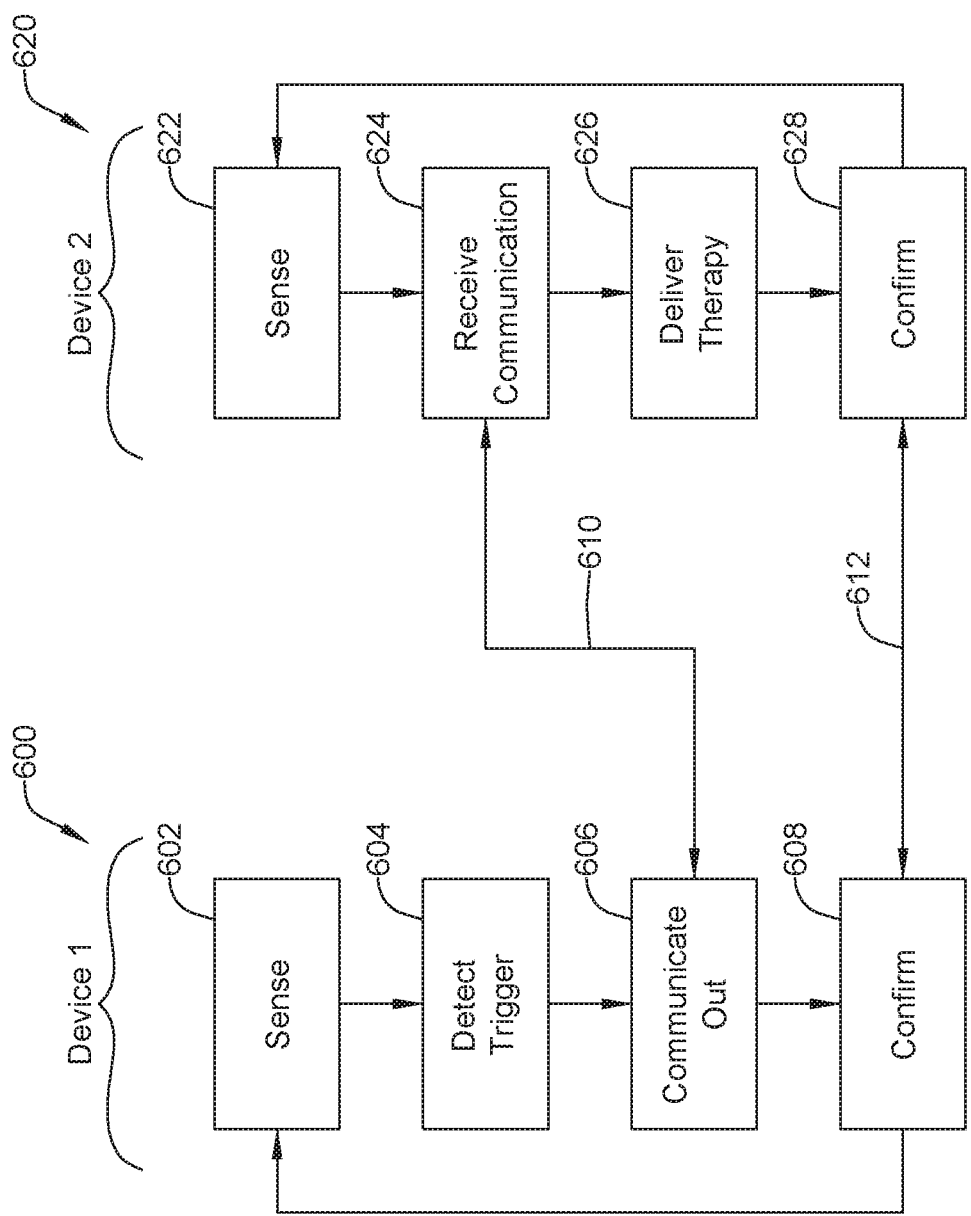
FIG. 11 shows in block flow form operation of cooperating devices.

FIG. 11 shows in block flow form operation of two cooperating devices. A first device performs operations as shown at 600, while a second device performs operations as shown at 620. Communications between the device are shown at 610, 612, though it should be understood that additional back and forth communication may also take place during device operations.

At a first point in time, each device is sensing for cardiac activity, as shown at 602, 622. For example, during block 602, Device 1 (which may be an SICD or subcutaneous cardiac monitoring device), may perform sensing for ventricular and/or atrial events, such as observing for R-waves, T-waves, or P-waves. Device 2 (which may be an LCP), may or may not perform sensing. In some examples, Device 2 may omit sensing and may instead simply rely upon Device 1 for therapy directions. In other examples, both devices sense for cardiac (or other) activity. For example, in block 622, Device 2 may observe whether a ventricular extrasystole event such as a premature ventricular contraction (PVC) occurs, or whether the ventricles otherwise "beat" before an atrial event is detected. (see FIG. 18, below for such exception handling).

At 604, Device 1 detects a trigger. The trigger may be, for example, an atrial event such as a P-wave. For example, the P-wave may be detected during a P-wave detection window, or may be detected by comparing a received signal to a template. If desired, the P-wave may be both detected and confirmed by using a detection method (comparing to an amplitude during a P-wave window, for example) and a confirmation method (comparing a possible P-wave signal to a template).

Device 1 then communicates out, as shown at 606, issuing a communication to Device 2, which is then received at Device 2. The communication may command or request a therapy delivery, or may indicate that a P-wave has been detected. For example, in a Master-Slave relationship, Device 2 may receive a command for pacing therapy and simply respond by generating a pacing output. In other interactions, Device 2 may receive a request for therapy delivery and proceed to deliver the requested therapy unless an exception arises before or after the request is received. In yet another interaction, Device 2 may receive an indication that a P-wave has been observed by Device 1, and Device 2 may then determine whether pacing or other therapy is appropriate.

After receiving the communication at 624, in the example shown, Device 2 delivers therapy at 626. Either or both of the two devices may, optionally, confirm that therapy was effective at 608 and 628. This confirmation may be communicated between the devices, as indicated at 612. For example, Device 1 may confirm that therapy was effective by observing the morphology of the cardiac signal following therapy delivery using, for example, a paced beat template. Device 2 may confirm that therapy was effective by observing morphology or by any other suitable manner. Alternatively, communication 612 may be omitted. For example, Device 1 may restart its sensing cycle following detection of an evoked response to therapy 626, or after detecting therapy 626; Device 2 may restart its sensing cycle following delivery of therapy 626.

While only two devices are represented in FIG. 11, additional devices may be involved. For example, a third device may be an LCP that functions similar to Device 2. For example, a first LCP may have a right ventricular location and a second LCP may have a left ventricular location, allowing biventricular pacing to be delivered, with both LCP devices generating therapy output relying for timing information upon Device 1's detection of an atrial event. If two LCP devices are included, each may be separately programmed to delay therapy 626 from the trigger detected at 604 to achieve desirable resynchronization characteristics. Such timing, either with a single or plural LCP devices involved, may be addressed in part using methods illustrated by FIGS. 12A-12B.

Figures 12A, 12B:
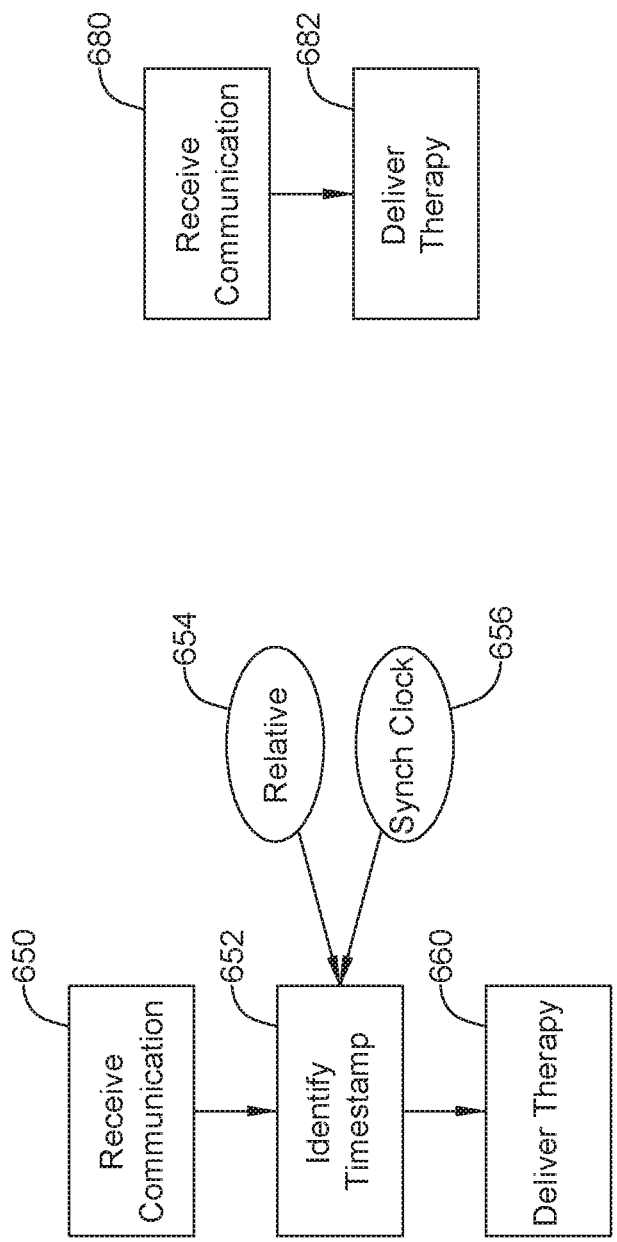
FIGS. 12A-12B illustrate different manners of handling cross-device timing.

FIGS. 12A-12B illustrate different manners of handling cross-device timing. In this example, the operation of an LCP is illustrated in which the LCP receives a communication at 650. The communication includes a timestamp associated with the time at which a therapy trigger was identified by the SICD, which timestamp is extracted from the communication in block 652. The timestamp may be a relative timestamp as indicated at 654. A relative timestamp may be based on a system event such as the point in time of a prior communication, or of a prior therapy delivery as detected by the SICD. For example, the SICD may be capable of determining when a pacing pulse is delivered by the LCP, and may communicate the timing of a detected trigger relative to the LCP prior pacing pulse; in this way, the LCP need not synchronize its clock to the SICD and instead simply tracks when it last delivered a therapy. Alternatively, the timestamp may be based on a synchronization clock signal as indicated at 656, where one of the devices (LCP or SICD) includes a system clock to which each device is synchronized. Using the timestamp, the LCP determines when, relative to the trigger event, therapy should be delivered as indicated at 660.

FIG. 12B shows a somewhat simpler approach. A communication is received at 680, and therapy is delivered based at 682, without relying on a timestamp of the communication. Here, the LCP determines when it received the communication and determines when to deliver therapy based on the communication time. The method of FIG. 12B relies, in part, on an assumption that the time from a trigger event to communication is predictable and repeatable. As is known to those skilled in the art, communication retries can occur when a communication is issued but not acknowledged by the intended recipient. Retries would therefore potentially delay therapy in the method of FIG. 12B. To facilitate accuracy, the communication provided from the SICD may indicate whether it is the first communication in response to a given trigger, or whether it is a retry, such that the LCP can adjust its timing according to whether there have been one or more communication retries.

FIGS. 13-18 show in block flow format operations of two cooperating devices. As noted for FIG. 11, there may be more than just the two devices represented in these drawings, with additional LCP devices operating similar, in some examples, to "Device 2" of the Figures.

Figure 13:
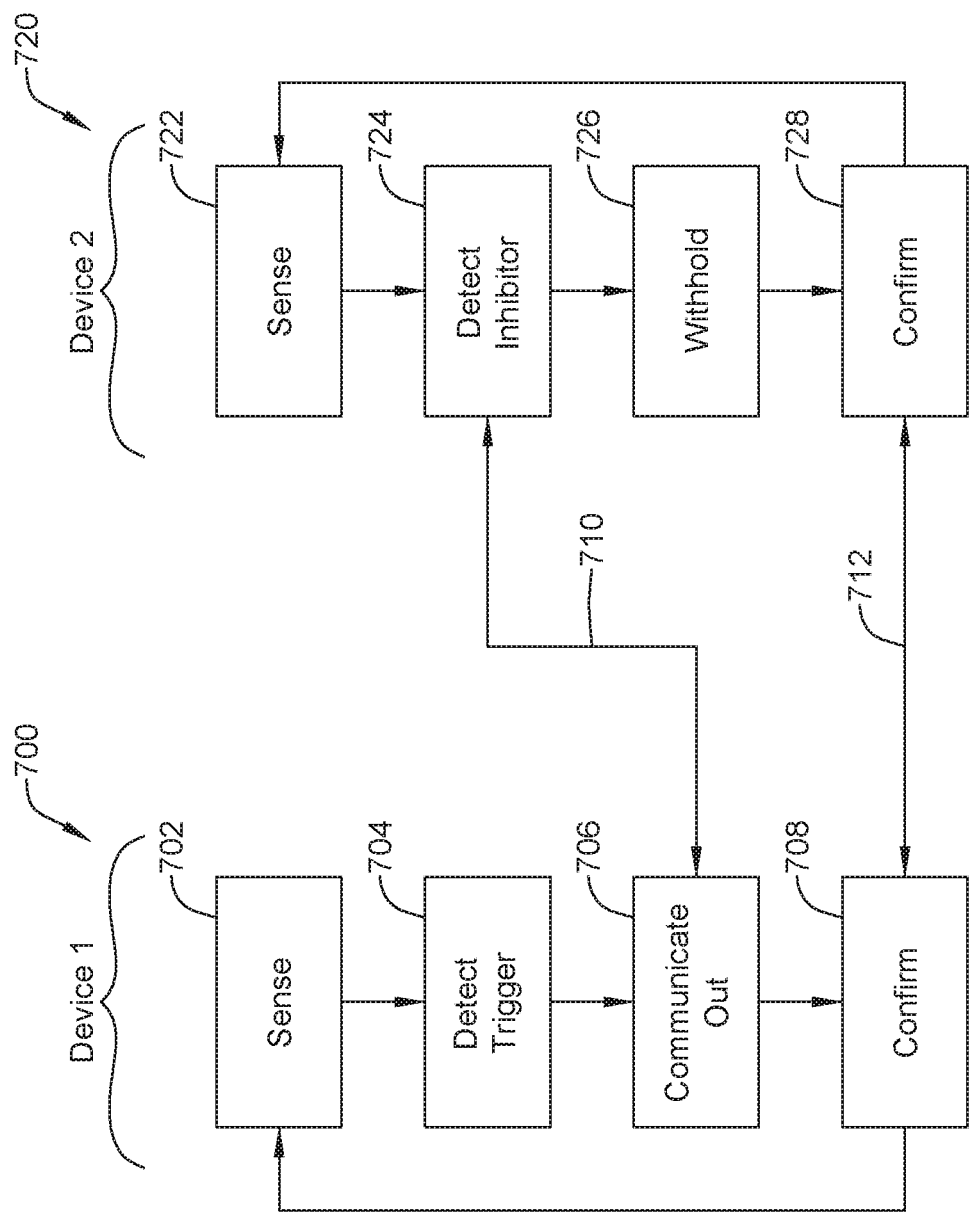
FIGS. 13-17 show in block flow form operations of cooperating devices.

FIG. 13 illustrates operations for Device 1 (which may be an SICD or a subcutaneous cardiac monitor) at 700 and Device 2 (which may be an LCP) at 720. In this example, each of the devices sense obtained signals looking to detect one or more predefined events. Device 1 detects a trigger event, such as an atrial event or P-wave, as indicated at 704. However, Device 2 also detects an inhibiting event as indicated at 724. An inhibiting event may be, for example, a QRS complex or an R-wave, or a PVC. Such detection at 724 may occur by, for example, comparing received signals against a threshold defined at a high enough amplitude to pass over typical P-waves and/or T-waves. The presence of the inhibitor at 724 causes Device 2 to withhold therapy as shown at 726 in this example. Thus, when Device 1 communicates out at 706 in response to detecting the trigger at 704, Device 2 may respond to the communication at 710 by ignoring it, or by providing a response to Device 1 to indicate that no therapy will be delivered due to the inhibitor having been detected. The two devices may, as before, confirm status at 708, 728, with or without communication 712 therebetween.

Figure 14:
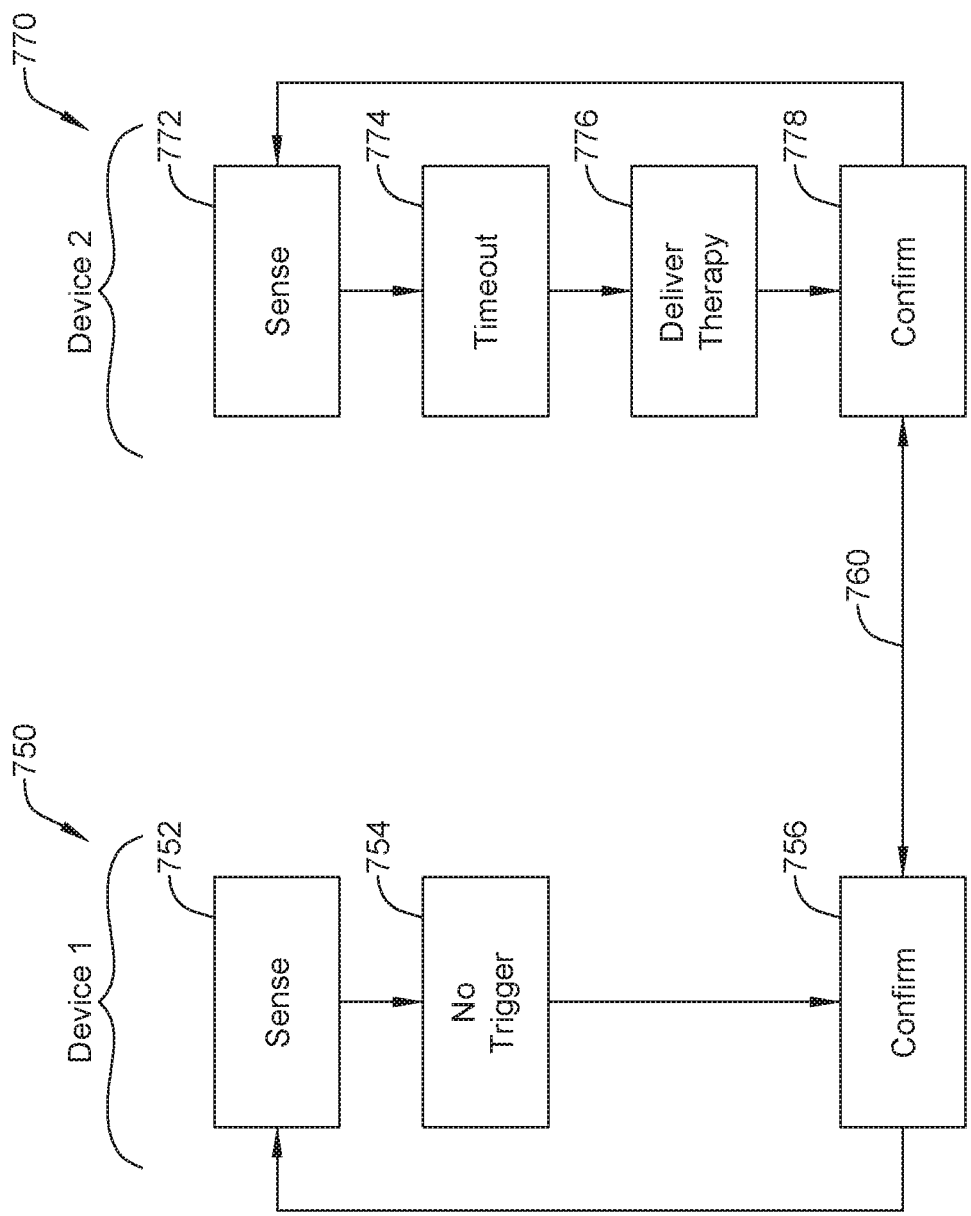

FIG. 14 shows another example with operations for Device 1, which may be an SICD or a subcutaneous cardiac monitor, shown at 750, and for Device 2, which may be an LCP, at 770. Here, Device 1 applies its sensing for a trigger at 752, however, no trigger is detected at 754. Device 2 also senses at 772, but encounters a timeout without detecting an inhibiting event and without receiving a communication from Device 1 indicating that therapy should be delivered. Such a scenario may, in some examples, inhibit therapy entirely. In this example, however, Device 2 delivers therapy at 776 in response to a timeout at 774. The timeout 774 may occur if a relevant escape interval expires for a patient who is both pace dependent and receiving CRT, for example.

Again the devices may confirm status at 756, 778 with or without communication therebetween at 760.

Figure 15:
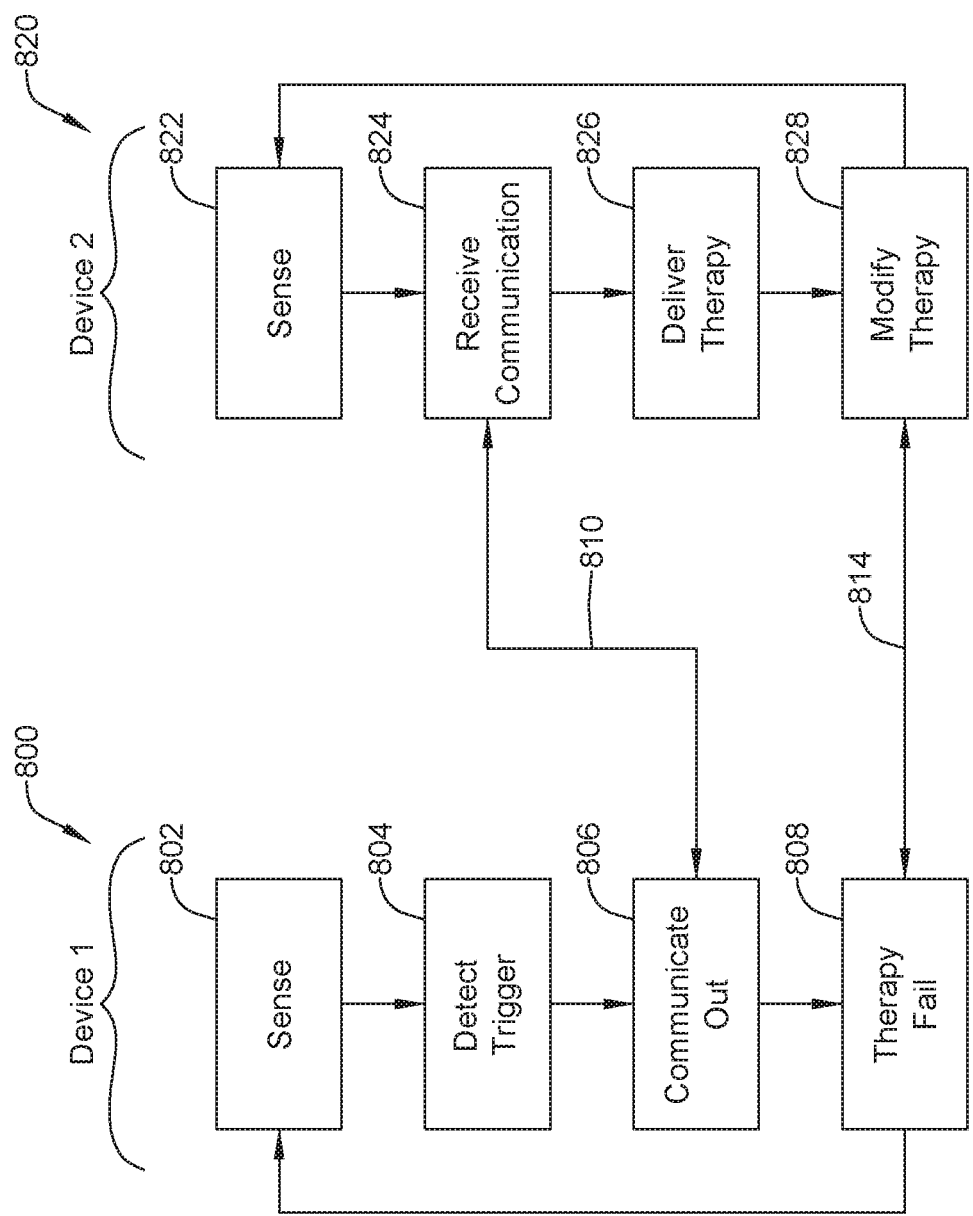

FIG. 15 shows another example with operations for Device 1, which may be an SICD or a subcutaneous cardiac monitor, shown at 800, and for Device 2, which may be an LCP, at 820. Each of Device 1 and Device 2 apply sensing parameters at 802, 822, respectively. Device 1 detects a trigger at 804 and communicates out to Device 2 at 806, commanding or requesting therapy, or simply indicating presence of the trigger 804. Device 2 receives communication 810 at 824, and then delivers therapy 826 in response to (and after a determined delay relative to) the trigger. In this example, however, Device 1 continues sensing after the Communication out at 806, and determines that therapy failed to capture the heart. Such failure may be determined by either the absence of an R-wave or QRS complex in response to the therapy 825, or by analyzing the R-wave or QRS complex that does occur and determining it does resemble a captured beat (by for example determining a capture template is not matched), or that it occurred at a time indicating no capture (that is, the responsive contraction may occur too late or too early to have been a response to the stimulus).

In the example of FIG. 15, the therapy failure 808 is then communicated to Device 2, which modifies therapy at 828. Therapy modification 828 may include, for example, changing therapy amplitude, pulse width or other shape/energy characteristic, changing the timing of therapy by increasing or reducing a delay from the trigger, changing a therapy polarity, polarity type, or electrode configuration, or by changing other suitable therapy characteristic(s). The specific therapy modification 828 may be determined by either of Device 1 or Device 2. In this example, following non-capture, the devices return to sensing. Device 2, in this example, may store new pacing parameters for use in a next iteration.

Figure 16:
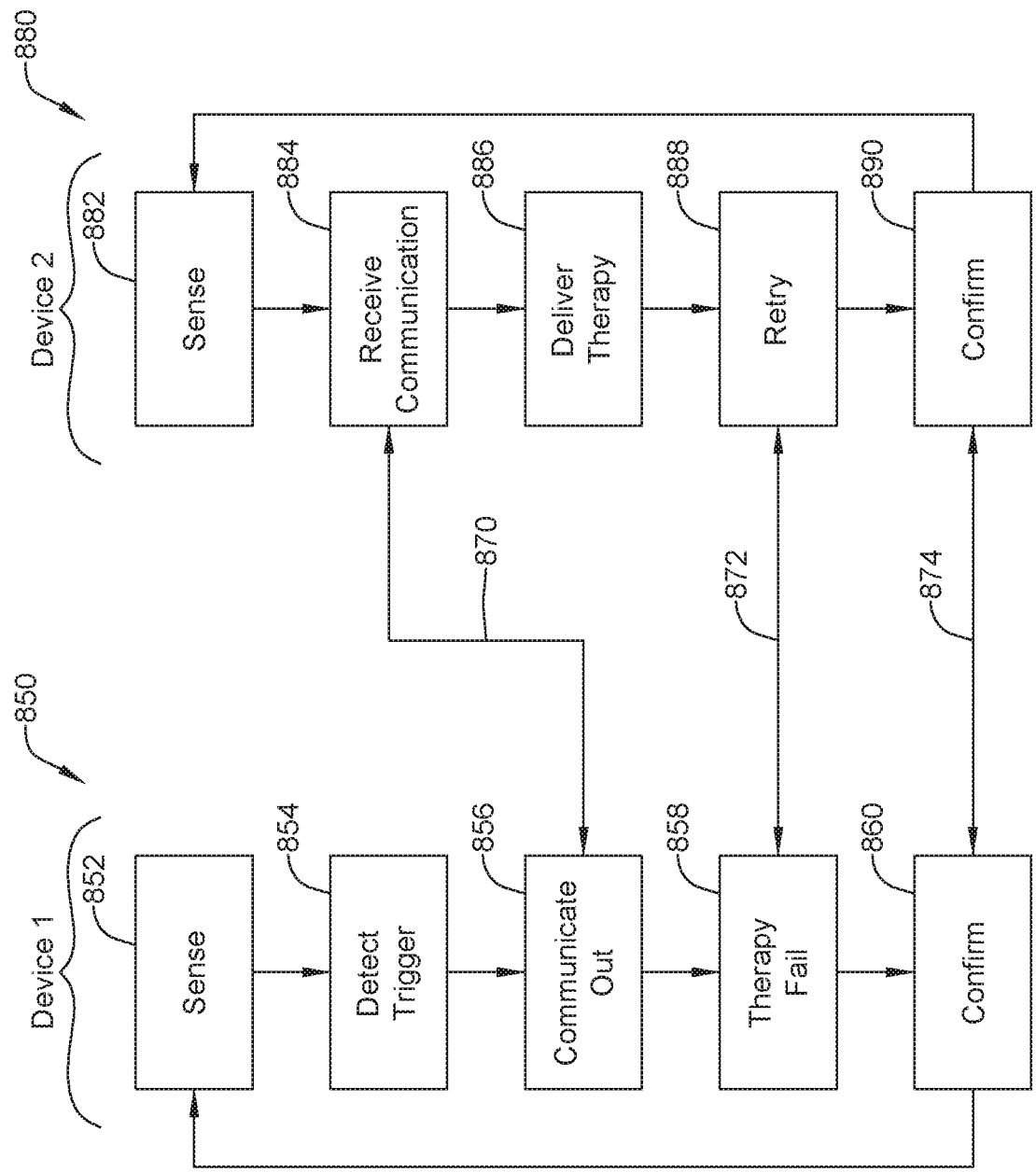

FIG. 16 shows an alternative to FIG. 15. Operations for Device 1, which may be an SICD or a subcutaneous cardiac monitor, are shown at 850. Operations for Device 2, which may be an LCP, are shown at 880. Each of Device 1 and Device 2 apply sensing parameters at 852, 882, respectively. Device 1 detects a trigger at 854 and communicates out to Device 2 at 856, commanding or requesting therapy, or simply indicating presence of the trigger 854. Device 2 receives communication 870 at 884, and then delivers therapy 886 in response to (and after a determined delay relative to) the trigger.

In the example of FIG. 16, however, Device 1 continues sensing after the Communication out at 856, and determines that therapy failed to capture the heart as indicated at 858. Here, it would be determined that there was no response to therapy 886 and the heart has not yet had a contraction. A communication is issued at 872 in response to the finding that therapy failed at 858, and therapy is retried at 888 by Device 2. Plural retries may take place, and the retry of therapy may occur with changed parameters including increasing amplitude and/or pulse width, changing polarity, polarity type or electrode configuration, or by changing other suitable therapy characteristic(s). Once a beat occurs, either through capture or intrinsic, the devices confirm that the heart beat took place at 860, 890, with or without communication therebetween 874. Device 2, in this example, may store new pacing parameters for use in a next iteration. The scenario of FIG. 16 is less likely to be needed in many CRT patients; instead, those who are pacemaker dependent, for example having an AV block, may benefit by use with right ventricular placed LCP (see item 40, FIG. 1).

Figure 17:
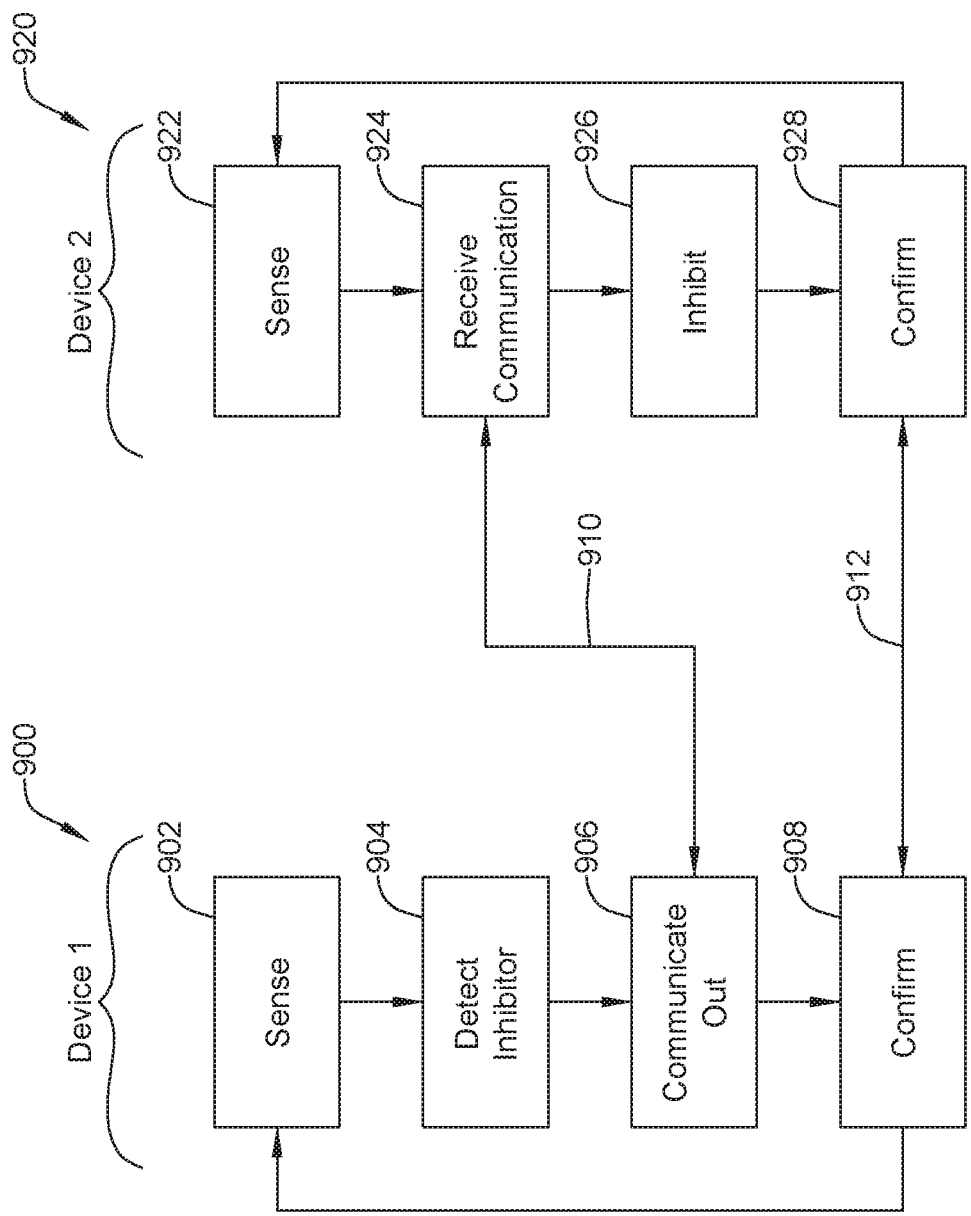

FIG. 17 shows another illustrative example. Operations for Device 1, which may be an SICD or a subcutaneous cardiac monitor, are shown at 900. Operations for Device 2, which may be an LCP, are shown at 920. Each of Device 1 and Device 2 apply sensing parameters at 902, 922, respectively. Device 1 detects an inhibitor at 904 which may be, for example, a QRS complex, an R-wave, or a PVC. In some examples, Device 1 may detect an inhibitor 904 as a premature atrial contraction (PAC). In response to the inhibitor, as shown at 906, Device 1 may generate a communication 910 to Device 2. Device 2 receives the communication at 924, and inhibits therapy as indicated at 926. The two devices may confirm status at 908, 928, with or without communication 912 therebetween. The scenario of FIG. 17 may arise, for example, if Device 2 is configured to deliver therapy at a given interval absent an inhibition command.

For each of FIGS. 13 and 17, special parameters may be applied following the identification of an inhibiting event for use in a subsequent cycle, as contrasted to parameters for use following a pace-captured beat. For example, following an inhibiting event, parameters for sensing may be modified to use different periods and fiducials for the starting point of timeouts. Referring briefly to FIG. 7, for example, the following may change depending on whether an intrinsic beat (shown at 302) or paced beat (shown at 332) occurs:

- The first delay period 314 may be different from the second delay period 340;
- The first P-wave detection window 316 may use different duration, filtering, or detection parameters (such as amplitude or slope thresholds, or P-wave template) than the second P-wave detection window 342;
- The first delay 322 may be different from the second delay 346 preceding pacing therapy delivery; and/or
- The first pacing therapy 324 may have different amplitude, polarity, polarity type, pulse width or other parameters from the second pace therapy 348

A third (or more) set of parameters may apply to any of these variables in the event that a PVC or PAC occurs, rather than a QRS complex. Additional exception rules may be defined if, for example, some element of a fiducial or detection window encounters an unusual event. For example, if using the T-wave peak as a fiducial for timing a P-wave detection window, the T-wave peak may be required to demonstrate certain characteristics such as a minimum amplitude, or a particular polarity, to be deemed suitable as the fiducial. If the fiducial event does not occur in an expected manner, additional exception rules may apply.

Figure 18:
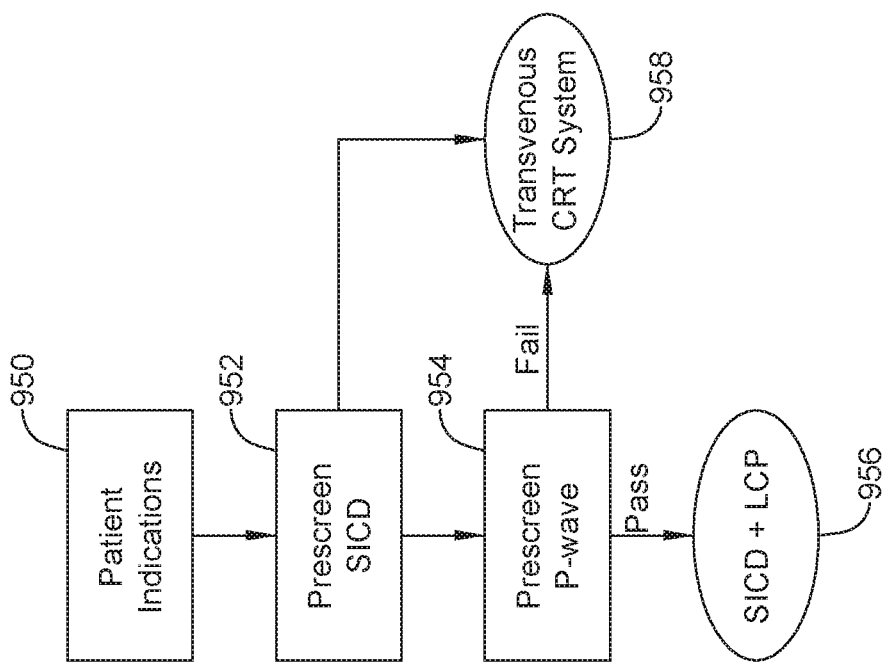
FIG. 18 shows a pre-implantation process flow.

FIG. 18 shows a pre-implantation process flow. A patient having appropriate indications for CRT is first identified as indicated at 950. Such indications are well known in the art any may include, for example, a wide QRS complex, left bundle branch block, the New York Heart Association Functional Classifications, as well as information about comorbidities. The patient may undergo prescreening for adequacy of cardiac signals as captured by the SICD, as indicated at 952. Step 952 may, for example, use tools, metrics and methods discussed in U.S. Pat. No. 8,079,959, titled PATIENT SCREENING TOOLS FOR IMPLANTABLE CARDIAC STIMULUS SYSTEMS, and/or U.S. patent application Ser. No. 15/001,976, titled AUTOMATED SCREENING METHODS AND APPARATUSES FOR IMPLANTABLE MEDICAL DEVICES, the disclosures of which are incorporated herein by reference. For example, the size and/or consistency of the R-wave and/or the signal to noise ratio of the cardiac signal may be observed, or the ability of an implantable device algorithm to correctly analyze obtained cardiac signals may be determined prior to implantation by applying an algorithm that the device would use once implanted to signals obtained before implantation. A similar process may then be repeated with respect to the P-wave, as indicated at 954. If both prescreens pass, then the patient may receive a combination of SICD and LCP, as indicated at 956. If either of the prescreens 952, 954 fail, then the patient may be implanted with a transvenous CRT system as indicated at 958.

Other combinations may arise; for example, the patient may pass the SICD screening and could then receive a CRT-P device transvenously, paired with the SICD. In such a system, the CRT-P device and SICD may communicate with one another as desired including in some examples the above methods for using the SICD to assist in determining whether and when the CRT-P would provide pacing therapy in one or more chambers of the heart.

Following are a number of illustrative examples indicating a manner in which various means may be defined in the context of the present invention.

A first illustrative example may take the form of an implantable device system comprising a first medical device (14, 40) comprising pacing means for delivering a pacing therapy to the heart of a patient, and a second medical device (16) comprising sensing means to sense activity of the heart of the patient. The pacing means may comprise a controlling output digital to analog converter (using either voltage or current control) configured to deliver an output current or voltage via output circuitry of an implantable device, such as illustrated with the pulse generator module 104 in FIG. 3, for coupling to one or several of the electrodes 114, 116, and/or 118. The sensing means may comprise processing circuitry including, for example, filtering, amplifying and, as needed, analog-to-digital converting circuitry 52, coupled via input/output circuitry 58 to one or several electrodes such as electrodes on a canister/housing shown at 64, 66 and/or at 72 on lead 70, all of which are shown in FIG. 2.

Further in the first illustrative example, the first medical device also comprises first communications means for at least receiving communications from at least the second medical device, and the second medical device comprises second communications means for at least issuing communications to at least the first medical device. The first communications means may include amplifying, modulating, demodulating, and/or processing circuitry making up a communications module 102 that may use an antenna and/or electrodes 114, 116 and/or 118 for either radiative or conducted communications, all shown in FIG. 3. The second communications means may include amplifying, modulating, demodulating and/or processing circuitry making up communications block 62, that may in turn use one or more of an antenna 74 and/or electrodes 64, 66 and/or 72 for communication, all shown in FIG. 2.

Further in the first illustrative example, the second medical device comprises atrial event means for using the sensing means to detect an atrial event in the heart of the patient and, in response thereto, to issue a communication to the first medical device. Such atrial event means may take the form of instruction sets stored in memory 54 for operation by a processing block 52 which may include a microcontroller, microprocessor, state machine, or other control, logic and/or processing circuitry, all shown in FIG. 2. The instruction sets for atrial event means may comprise instructions for sensing 602, detecting a trigger 604 and communicating out 606, as shown in FIG. 11, as well as analogous operational blocks of FIGS. 13-17 (here the second medical device in the first illustrative example may operate as "Device 1" in any of FIGS. 11 and 13-17).

Finally in the first illustrative example, the first medical device comprises therapy means for using the pacing means to deliver therapy to the heart of the patient in response to the communication means receiving the communication issued by the second medical device. The therapy means may take the form of operational instructions for execution by a processing module as shown at 110, operatively coupled to a communications module 102 and the pulse generator module 104, all as shown in FIG. 3. The operational instructions for the therapy means may comprise instructions for receiving a communication 624 and delivering therapy 626 as shown in FIG. 11, as well as analogous operational blocks of FIGS. 13-17 (here the first medical device in the first illustrative example may operate as "Device 2" in any of FIGS. 11 and 13-17).

A second illustrative example takes the form of a system as in the first illustrative example, wherein the second medical device comprises initialization means for initializing the second medical device atrial event means, including: detection means for detecting at least first and second cardiac cycles of the patient; and window means for establishing a window for detection of the atrial event; wherein the atrial event means is configured to observe cardiac signals of the patient during the window for detection of the atrial event in order to detect the atrial event. In this second illustrative example, the initialization means may take the form of instruction sets stored in memory 54 for operation by a processing block 52 which may include a microcontroller, microprocessor, state machine, or other control, logic and/or processing circuitry, in which instructions the processing block 52 may control and/or access I/O block 58 to use system electrodes 64, 66 and/or 72, all shown in FIG. 2. Such instructions for the initialization means may operate to execute as shown in FIG. 9, using detection means instructions that operate as shown by one or both of 454 and 460 to obtain data as indicated at 562, and then setting parameters including, for example, a window for P-wave detection as indicated at 484. FIGS. 10A-10B show additional versions of the initialization means instruction sets, including obtaining data and setting brady/CRT sensing parameters 504 and/or atrial sensing parameters 514. FIGS. 5A, 5C and 5D each show illustrative approaches to the use of such windows 176 (FIG. 5A), 230 (FIG. 5C), and 242 (FIG. 5D).

In additional sub-examples related to the second illustrative example, the detection means may be configured to calculate a composite cardiac cycle data set using the at least first and second cardiac cycles; and the window means may be configured to establish the window for detection of the atrial event using the composite cardiac cycle data set, such as illustrated at 460, 462, 464 in FIG. 9. In yet another sub-example, the window means is configured to set timing information for the window for detection using at least one of the following factors: a feature of a ventricular event detected by the sensing means; or occurrence of a therapy output by the first medical device; FIG. 7 illustratively shows the use of ventricular event (R-wave 312) as such a fiducial. Again, these sub-examples may be embodied in operational instructions for operation by a processing block 52 and associated circuitry including I/O block 58 in FIG. 2.

In a third illustrative example, the initialization means of the second illustrative example comprises event characterizing means for determining characteristics of the atrial event, the characteristics comprising at least one of: an amplitude; a relative amplitude as compared to one or more preceding ventricular events; a relative amplitude as compared to a mean amplitude during a cardiac cycle; or a maximum or minimum slope; wherein the atrial event means is configured to use determined characteristics of the atrial event in order to detect the atrial event. Such features 486 (FIG. 9) may be selected and used according to operational instructions for operation by a processing block 52 (FIG. 2), to execute a method as illustrated in at least FIG. 9.

In another illustrative example, the atrial event means of the first or second illustrative examples comprises comparison means to determine whether a signal captured during the window for detection of the atrial event matches a stored atrial event template or a dynamic atrial event template and conclude whether an atrial event occurs in the window for detection using results of the comparison. Such comparison means may be embodied in a processing block 52 (FIG. 2) configured to execute instructions for performance as shown in FIG. 5D.

In an illustrative example, the second medical device of any of the first, second or third illustrative examples comprises a plurality of electrodes configured for use in sensing cardiac signals, and the second medical device comprises vector selecting means comprising: ventricular signal vector means configured to analyze signals from a plurality of sensing vectors defined by the plurality of electrodes and select a first sensing configuration for detection of ventricular events; and atrial signal vector means configured to analyze signals from a plurality of sensing vectors defined by the plurality of electrodes and select a second sensing configuration for detection of atrial events. The vector selection means may take the form of instruction sets stored in memory 54 for operation by a processing block 52 which may include a microcontroller, microprocessor, state machine, or other control, logic and/or processing circuitry, controlling switches in the I/O block 58 all shown in FIG. 2, with the instruction sets configured to execute a method as shown in FIG. 10B. Such an example may be designed such that the atrial event means is configured to determine one or more parameters for sensing of atrial events using the second sensing configuration, and/or such that the atrial event means is configured to establish a template for atrial events to use to determine whether a signal captured using the second sensing configuration is an atrial event of a predetermined type.

Any of the first to third illustrative examples may be selectively operable to treat Bradycardia, and/or to improve cardiac synchronization. Moreover, such illustrative examples may be configured to allow the second medical device to indicate using the communication means that it has detected an atrial event, and wherein the therapy means is configured to determine when therapy is to be delivered relative to timing of the atrial event. In addition, in some further examples, the second medical device has second communication means having operational instructions configured to command delivery of therapy by the first medical device at a particular time.

These illustrative examples may include a system wherein the first medical device is a leadless cardiac pacemaker, and the second medical device is an implantable cardiac monitor. Alternatively, these illustrative examples may include a system wherein the first medical device is a leadless cardiac pacemaker, and the second medical device is a subcutaneous implantable defibrillator.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose a specific order of steps in a process, or any numerical requirements on their objects. Where a specific order of a steps is intended in the claims, the words "before" or "after" will be used.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device comprising:
   a lead comprising a plurality of implantable electrodes including at least first and second sensing electrodes;
   a housing containing operational circuitry for analyzing signals captured using the plurality of implantable electrodes, the housing also including at least one electrode, the operational circuitry further comprising communication circuitry configured to communicate to a second implantable medical device;
   wherein the operational circuitry is configured to perform a sensing vector selection routine in which:
      the operational circuitry performs a first analysis of signals from a plurality of sensing vectors defined by the plurality of electrodes and selects a first sensing configuration having a first sensing vector from the plurality of sensing vectors for detection of ventricular events; and
      the operational circuitry performs a second analysis of signals from the plurality of sensing vectors defined by the plurality of electrodes and selects a second sensing configuration having a second sensing vector from the plurality of sensing vectors for detection of atrial events; and
   further wherein:
   the operational circuitry is configured to use the second sensing configuration to determine whether an atrial event is detected; and
   in response to determining that an atrial event has been detected, the operational circuitry is configured to communicate to the second medical device.

2. The implantable medical device of claim 1 wherein the operational circuitry is configured to determine an atrial sensing window for detection of atrial events and is configured to selectively use the second sensing configuration to determine whether an atrial event takes place in the atrial sensing window, wherein the operational circuitry is configured to define the atrial sensing window in relationship to a ventricular sensed event sensed identified using the first sensing configuration.

3. The implantable medical device of claim 1 wherein the operational circuitry is configured to determine an atrial sensing window for detection of atrial events and is configured to selectively use the second sensing configuration to determine whether an atrial event takes place in the atrial sensing window, wherein the operational circuitry is configured to define the atrial sensing window in relationship to a detected therapy output generated by the second medical device.

4. The implantable medical device of claim 1 wherein the operational circuitry further comprises therapy delivery circuitry to issue electrical cardiac therapy, and the operational circuitry is configured to use the first sensing configuration to sense ventricular arrhythmia, and when a ventricular arrhythmia is detected, to use the therapy delivery circuitry to issue a therapy for ventricular arrhythmia.

5. The implantable medical device of claim 1 wherein the operational circuitry is configured to use the first sensing configuration to sense ventricular arrhythmia, and when a ventricular arrhythmia is detected, to issue a communication to the second medical device to treat ventricular arrhythmia.

6. The implantable medical device of claim 1 wherein the operational circuitry is configured to use the second sensing configuration to sense events to support bradycardia therapy.

7. The implantable medical device of claim 1 wherein the operational circuitry is configured to use the second sensing configuration to sense events to support resynchronization therapy.

8. An implantable medical device comprising:
   a housing having a plurality of implantable electrodes thereon and containing operational circuitry for analyzing signals captured using the plurality of implantable electrodes, the operational circuitry further comprising communication circuitry configured to communicate to a second implantable medical device;
   wherein the operational circuitry is configured to perform a sensing vector selection routine in which:
      the operational circuitry performs a first analysis of signals from a plurality of sensing vectors defined by the plurality of electrodes and selects a first sensing configuration having a first sensing vector from the plurality of sensing vectors for detection of ventricular events; and
      the operational circuitry performs a second analysis of signals from the plurality of sensing vectors defined by the plurality of electrodes and selects a second sensing configuration having a second sensing vector from the plurality of sensing vectors for detection of atrial events; and
   further wherein:
   the operational circuitry is configured to use the second sensing configuration to determine whether an atrial event is detected; and
   in response to determining that an atrial event has been detected, the operational circuitry is configured to communicate to the second medical device.

9. The implantable medical device of claim 8 wherein the operational circuitry is configured to determine an atrial sensing window for detection of atrial events and is configured to selectively use the second sensing configuration to determine whether an atrial event takes place in the atrial sensing window, wherein the operational circuitry is configured to define the atrial sensing window in relationship to a ventricular sensed event sensed identified using the first sensing configuration.

10. The implantable medical device of claim 8 wherein the operational circuitry is configured to determine an atrial sensing window for detection of atrial events and is configured to selectively use the second sensing configuration to determine whether an atrial event takes place in the atrial sensing window, wherein the operational circuitry is configured to define the atrial sensing window in relationship to a detected therapy output generated by the second medical device.

11. The implantable medical device of claim 8 wherein the operational circuitry is configured to use the first sensing configuration to sense ventricular arrhythmia, and when a ventricular arrhythmia is detected, to issue a communication to the second medical device to treat ventricular arrhythmia.

12. The implantable medical device of claim 8 wherein the operational circuitry is configured to use the second sensing configuration to sense events to support bradycardia therapy.

13. The implantable medical device of claim 8 wherein the operational circuitry is configured to use the second sensing configuration to sense events to support resynchronization therapy.

14. An implantable medical device comprising:
- a housing containing operational circuitry for analyzing cardiac signals and communication circuitry configured to communicate to a second implantable medical device;
- a plurality of electrodes coupled to the operational circuitry to provide cardiac signals thereto, the plurality of electrodes including at least one electrode on the housing and at least two additional electrodes that are disposed on the housing or on a lead;
- wherein the operational circuitry is configured to perform a sensing configuration routine in which:
  - the operational circuitry performs a first analysis of signals from the plurality of electrodes and selects a first sensing configuration for detection of ventricular events; and
  - the operational circuitry performs a second analysis of signals from the plurality of electrodes and selects a second sensing configuration for detection of atrial events; and
- further wherein:
  - the operational circuitry is configured to use the second sensing configuration to determine whether an atrial event is detected; and
  - in response to determining that an atrial event has been detected, the operational circuitry is configured to communicate to the second medical device.

15. The implantable medical device of claim 14 wherein the operational circuitry is configured to determine an atrial sensing window for detection of atrial events and is configured to selectively use the second sensing configuration to determine whether an atrial event takes place in the atrial sensing window, wherein the operational circuitry is configured to define the atrial sensing window in relationship to a ventricular sensed event sensed identified using the first sensing configuration.

16. The implantable medical device of claim 14 wherein the operational circuitry is configured to determine an atrial sensing window for detection of atrial events and is configured to selectively use the second sensing configuration to determine whether an atrial event takes place in the atrial sensing window, wherein the operational circuitry is configured to define the atrial sensing window in relationship to a detected therapy output generated by the second medical device.

17. The implantable medical device of claim 14 wherein the operational circuitry is configured to use the first sensing configuration to sense ventricular arrhythmia, and when a ventricular arrhythmia is detected, to issue a communication to the second medical device to treat ventricular arrhythmia.

18. The implantable medical device of claim 14 wherein the operational circuitry further includes a therapy delivery circuitry for issuing therapy to treat a ventricular arrhythmia, and is configured to use the first sensing configuration to sense ventricular arrhythmia, and when a ventricular arrhythmia is detected, to treat the ventricular arrhythmia using the therapy delivery circuitry.

19. The implantable medical device of claim 14 wherein the operational circuitry is configured to use the second sensing configuration to sense events to support bradycardia therapy.

20. The implantable medical device of claim 14 wherein the operational circuitry is configured to use the second sensing configuration to sense events to support resynchronization therapy.

* * * * *